(12) United States Patent
Bass et al.

(10) Patent No.: US 12,403,044 B2
(45) Date of Patent: Sep. 2, 2025

(54) TISSUE TREATMENT DEVICE

(71) Applicant: T.J. Smith and Nephew, Limited, Hull (GB)

(72) Inventors: Mark Darren Bass, Sheffield (GB); Varuni Rachindra Brownhill, Swanland (GB); Anthony Dagger, York (GB); Neill John Rawson, Doncaster (GB); Iain Webster, Hull (GB)

(73) Assignee: T.J. Smith and Nephew, Limited, Hull (GB)

( * ) Notice: Subject to any disclaimer, the term of this patent is extended or adjusted under 35 U.S.C. 154(b) by 939 days.

(21) Appl. No.: 17/285,723

(22) PCT Filed: Oct. 15, 2019

(86) PCT No.: PCT/EP2019/077990
§ 371 (c)(1),
(2) Date: Apr. 15, 2021

(87) PCT Pub. No.: WO2020/079009
PCT Pub. Date: Apr. 23, 2020

(65) Prior Publication Data
US 2022/0001212 A1 Jan. 6, 2022

(30) Foreign Application Priority Data
Oct. 19, 2018 (GB) ..................... 1817052

(51) Int. Cl.
*A61F 13/00* (2024.01)
*A61F 13/05* (2024.01)
(Continued)

(52) U.S. Cl.
CPC ............. *A61F 13/05* (2024.01); *A61M 1/915* (2021.05); *A61N 7/00* (2013.01);
(Continued)

(58) Field of Classification Search
CPC ........................................................ A61N 7/00
See application file for complete search history.

(56) References Cited

U.S. PATENT DOCUMENTS

| 1,355,846 A | 10/1920 | Rannells |
| 3,367,332 A | 2/1968 | Groves |

(Continued)

FOREIGN PATENT DOCUMENTS

| EP | 2571467 A1 | 3/2013 |
| EP | 3173054 A1 | 5/2017 |

(Continued)

OTHER PUBLICATIONS

International Preliminary Report on Patentability for Application No. PCT/EP2019/077990, mailed on Apr. 29, 2021, 9 pages.
(Continued)

*Primary Examiner* — Joseph M Santos Rodriguez
(74) *Attorney, Agent, or Firm* — Knobbe, Martens, Olson & Bear, LLP

(57) ABSTRACT

Disclosed embodiments relate to apparatuses and methods for wound treatment with ultrasound. In certain embodiments, a therapeutic ultrasound wound treatment apparatus includes a wound dressing configured to be positioned over a wound to provide a substantially fluid impermeable seal over the wound and a transducer to deliver therapeutic ultrasound to tissue. The therapeutic ultrasound wound treatment apparatus may further include a wound contact layer configured to be positioned in contact with the wound, a transmission layer positioned above the wound contact layer, an absorbent layer positioned above the transmission layer and configured to absorb wound fluid, and a backing layer positioned above the absorbent layer and including an orifice. Also disclosed are multiple parameters for the therapeutic ultrasound signal.

7 Claims, 31 Drawing Sheets

(51) Int. Cl.
*A61M 1/00* (2006.01)
*A61N 7/00* (2006.01)

(52) U.S. Cl.
CPC ...... *A61F 2013/0028* (2013.01); *A61M 1/982* (2021.05); *A61M 1/985* (2021.05); *A61M 2205/058* (2013.01); *A61N 2007/0017* (2013.01)

(56) References Cited

U.S. PATENT DOCUMENTS

| | | | |
|---|---|---|---|
| 4,466,431 | A | 8/1984 | Tharrat et al. |
| 4,530,360 | A | 7/1985 | Duarte |
| 4,787,888 | A | 11/1988 | Fox |
| 5,078,144 | A | 1/1992 | Sekino et al. |
| 5,112,323 | A | 5/1992 | Winkler et al. |
| 5,636,643 | A | 6/1997 | Argenta et al. |
| 5,904,659 | A | 5/1999 | Duarte et al. |
| 5,964,723 | A | 10/1999 | Augustine |
| 6,071,267 | A | 6/2000 | Zamierowski |
| 6,398,767 | B1 | 6/2002 | Fleischmann |
| 6,458,109 | B1 | 10/2002 | Henley et al. |
| 6,855,135 | B2 | 2/2005 | Lockwood et al. |
| 6,856,821 | B2 | 2/2005 | Johnson |
| 6,979,324 | B2 | 12/2005 | Bybordi et al. |
| 7,108,683 | B2 | 9/2006 | Zamierowski |
| 7,128,719 | B2 | 10/2006 | Rosenberg |
| 7,211,060 | B1 | 5/2007 | Talish et al. |
| 7,381,859 | B2 | 6/2008 | Hunt et al. |
| 7,524,315 | B2 | 4/2009 | Blott et al. |
| 7,532,953 | B2 | 5/2009 | Vogel |
| 7,569,742 | B2 | 8/2009 | Haggstrom et al. |
| 7,628,764 | B2 | 12/2009 | Duarte et al. |
| 7,699,830 | B2 | 4/2010 | Martin |
| 7,767,936 | B2 | 8/2010 | Ferguson |
| 7,794,438 | B2 | 9/2010 | Henley et al. |
| 7,794,450 | B2 | 9/2010 | Blott et al. |
| 8,075,503 | B2 | 12/2011 | Jaeb |
| 8,114,126 | B2 | 2/2012 | Heaton et al. |
| 8,162,909 | B2 | 4/2012 | Blott et al. |
| 8,298,200 | B2 | 10/2012 | Vess et al. |
| 8,372,049 | B2 | 2/2013 | Jaeb et al. |
| 8,529,578 | B2 | 9/2013 | Daniels et al. |
| 9,044,579 | B2 | 6/2015 | Blott et al. |
| 9,084,845 | B2 | 7/2015 | Adie et al. |
| 9,327,065 | B2 | 5/2016 | Albert et al. |
| 9,414,968 | B2 | 8/2016 | Heagle |
| 10,610,414 | B2 | 4/2020 | Hartwell et al. |
| 11,224,767 | B2 | 1/2022 | Loven et al. |
| 2002/0016570 | A1 | 2/2002 | Cartledge |
| 2002/0138036 | A1 | 9/2002 | Babaev |
| 2007/0248958 | A1 | 10/2007 | Jovanovich et al. |
| 2007/0286809 | A1 | 12/2007 | Williams et al. |
| 2008/0132821 | A1 | 6/2008 | Propp et al. |
| 2009/0192431 | A1 | 7/2009 | Horstmann et al. |
| 2009/0221977 | A1 | 9/2009 | Blott et al. |
| 2009/0312723 | A1 | 12/2009 | Blott et al. |
| 2010/0030132 | A1 | 2/2010 | Niezgoda et al. |
| 2010/0292632 | A1 | 11/2010 | Mulvihill et al. |
| 2010/0318052 | A1 | 12/2010 | Ha et al. |
| 2014/0024989 | A1 | 1/2014 | Ueda |
| 2014/0200487 | A1 | 7/2014 | Ramdas et al. |
| 2014/0296774 | A1 | 10/2014 | Bhavaraju et al. |
| 2014/0316359 | A1 | 10/2014 | Collinson et al. |
| 2015/0190286 | A1 | 7/2015 | Allen et al. |
| 2016/0120706 | A1 | 5/2016 | Collinson et al. |
| 2016/0325028 | A1 | 11/2016 | Locke et al. |
| 2017/0258386 | A1 | 9/2017 | Woltjer et al. |
| 2018/0093106 | A1 | 4/2018 | Binner et al. |
| 2018/0116877 | A1 | 5/2018 | Ineichen |
| 2018/0125722 | A1 | 5/2018 | Hoggarth et al. |
| 2018/0289870 | A1 | 10/2018 | Beasley et al. |
| 2018/0296397 | A1 | 10/2018 | Askem et al. |
| 2020/0008981 | A1 | 1/2020 | Wheldrake |
| 2020/0289856 | A1 | 9/2020 | Ogawa et al. |
| 2020/0315894 | A1 | 10/2020 | Churilla et al. |
| 2021/0001019 | A1 | 1/2021 | Elder et al. |
| 2021/0252314 | A1 | 8/2021 | Sverdlik et al. |
| 2022/0008112 | A1 | 1/2022 | Sverdlik et al. |

FOREIGN PATENT DOCUMENTS

| | | |
|---|---|---|
| KR | 20170001425 A | 1/2017 |
| WO | WO-9956829 A1 | 11/1999 |
| WO | WO-2015091376 A1 | 6/2015 |
| WO | WO-2016109420 A1 | 7/2016 |
| WO | WO-2020046847 A1 | 3/2020 |
| WO | WO-2020078993 A1 | 4/2020 |
| WO | WO-2020079009 A1 | 4/2020 |

OTHER PUBLICATIONS

Ennis W.J. et al., "Ultrasound Therapy for Recalcitrant Diabetic Foot Ulcers: Results of a Randomized, Double-Blind, Controlled, Multicenter Study—Part 1," Index: Ostomy Wound Manage., vol. 51, Issue 8, Aug. 2005, pp. 24-39.

Eriksson S.V., et al., "A Placebo Controlled Trial of Ultrasound Therapy in Chronic Leg Ulceration," Scand. J. Rehab. Med., vol. 23, 1991, pp. 211-213.

International Search Report and Written Opinion for Application No. PCT/EP2019/077990, mailed on Jan. 23, 2020, 15 pages.

Lundeberg T. et al., "Pulsed Ultrasound does not Improve Healing of Venous Ulcers," Scand. J. Rehab. Med., vol. 22, 1990, pp. 195-197.

Peschen M. et al., "Low-frequency Ultrasound Treatment of Chronic Venous Leg Ulcers in an Outpatient Therapy," Acta. Derm. Venereol (Stockh), 1997, vol. 77, pp. 311-314.

Riet G.T., et al., "Randomised clinical trial of ultrasound treatment for pressure ulcers," Department of Epidemiology, vol. 310, Apr. 22, 1995, pp. 1040-1041.

Weichenthal M. et al., "Low-frequency ultrasound treatment of chronic venous ulcers," Wound Repair and Regeneration, vol. 5, No. 1, Jan.-Mar. 1997, pp. 18-22.

Krishnasamy P.M., "Ultrasound Assisted Wound Care," Technology Review, Oct. 2005, 11 pages.

Oxford Learner's Dictionaries "absorb," Retrieved on Oct. 21, 2024, 4 pages, Retrieved from https://www.oxfordlearnersdictionaries.com/definition/english/absorb.

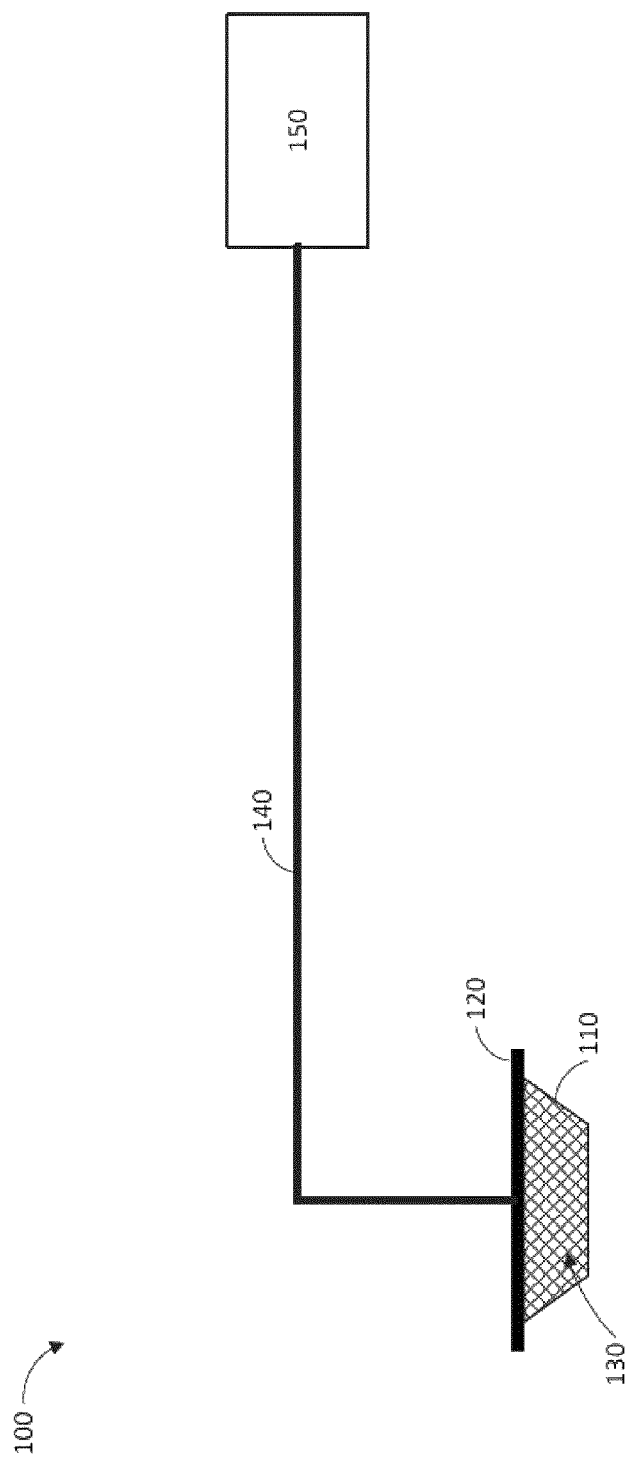

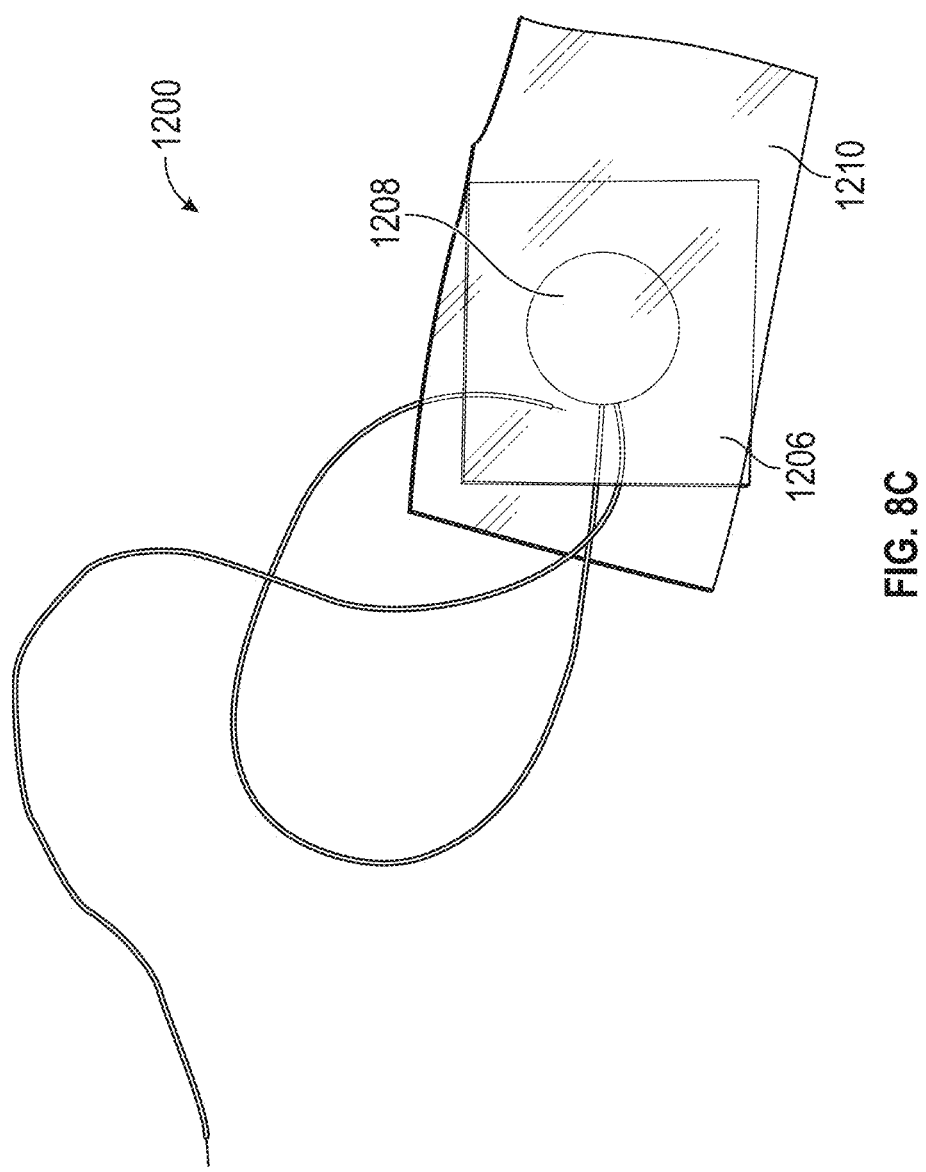

TISSUE TREATMENT DEVICE

CROSS-REFERENCE TO RELATED APPLICATIONS

This application is a U.S. national stage application of International Patent Application No. PCT/EP2019/077990, filed Oct. 15, 2019, which claims priority to U.K. Provisional Application No. 1817052.2, filed on Oct. 19, 2018; the disclosure of which is hereby incorporated by reference in its entirety.

BACKGROUND

Technical Field

Embodiments described herein relate to apparatuses, systems, and methods for the treatment of wounds with ultrasound.

Description of the Related Art

Chronic wounds and/or open wounds that do not heal within a normal timeframe are a significant problem amongst certain patient populations, particularly older patients that may have a compromised vasculature. Treatment of such wounds via application of negative pressure wound therapy (NPWT) to the wound site is well known in the art and numerous therapies exist. For example, NPWT systems and dressings such as PICO, RENASYS-F, RENASYS-G, RENASYS-AB, RENASYS-F/AB are currently available from Smith & Nephew.

The use of therapeutic ultrasound for the treatment of bone is also well known in the art. For example, the EXOGEN Ultrasound Bone Healing device by Bioventus is FDA-approved for accelerating the healing of bone fractures. However, application of therapeutic ultrasound to wounded tissue outside of bone is not well-known in the art, nor is the application of therapeutic ultrasound in combination with NPWT. Application of ultrasound to wounded tissue or unwounded tissue presents a number of complications, such as the proper mode of delivery and ideal signal parameters for healing intact and/or wounded tissue. Consequently, a proper vehicle for the delivery of therapeutic ultrasound to wounds is currently unknown.

Many different types of dressings are known in the art for use in wound healing. These different types of wound dressings include many different types of materials and layers, for example, gauze, pads, foam pads or multi-layer wound dressings. However, use of such dressings in combination with therapeutic ultrasound is not well-understood in the art, particularly due to the difficulties in transmitting therapeutic ultrasound through various mediums into tissue. Additionally, the optimum signal parameters for wound healing or for treating other types of tissues is not well-known.

Therefore, improved methods and techniques for delivering ultrasound to wounds and other tissues are needed.

SUMMARY

Certain disclosed embodiments relate to devices, methods, and systems for monitoring tissues. It will be understood by one of skill in the art that application of the devices, methods, and systems described herein are not limited to a particular tissue or a particular injury. Further embodiments are described below.

In certain embodiments, a method of treating a wound with vibrational energy may comprise:

applying vibrational energy to a wound from an ultrasonic transducer, the ultrasonic transducer positioned within an absorbent wound dressing; and controlling the ultrasonic transducer such that vibrational energy is delivered to the wound.

In certain embodiments, controlling the ultrasonic transducer may comprise controlling the ultrasonic transducer such that vibrational energy is delivered continuously to the wound for a period of time greater than 1 minute. The vibrational energy may be delivered continuously for at least about 20 minutes. In some embodiments, the vibrational energy may be pulsed to the wound.

The vibrational energy may comprise a duty factor of about 20%. The vibrational energy may be delivered at a frequency of about 1.5 MHz. The vibrational energy may be delivered at a frequency of about 1 MHz. In certain embodiments, the vibrational energy may be delivered at a frequency of about 3 MHz.

In embodiments, the vibrational energy may be delivered at an acoustic power of between about 2 mW/cm$^2$ to 6 mW/cm$^2$, such as about 3 mW/cm$^2$. The vibrational energy may be delivered at an acoustic power of between about 25 mW/cm$^2$ to 35 mW/cm$^2$, such as about 25 mW/cm$^2$.

In particular embodiments, the wound dressing may be covered with a cover layer. In certain embodiments, a therapeutic ultrasound wound treatment apparatus may comprise one or more features of the foregoing description.

BRIEF DESCRIPTION OF THE DRAWINGS

FIG. 1 illustrates a reduced pressure wound therapy system according to some embodiments.

FIGS. 8B-C are photographs of therapeutic ultrasound wound treatment apparatuses.

DETAILED DESCRIPTION

Figure 2A:
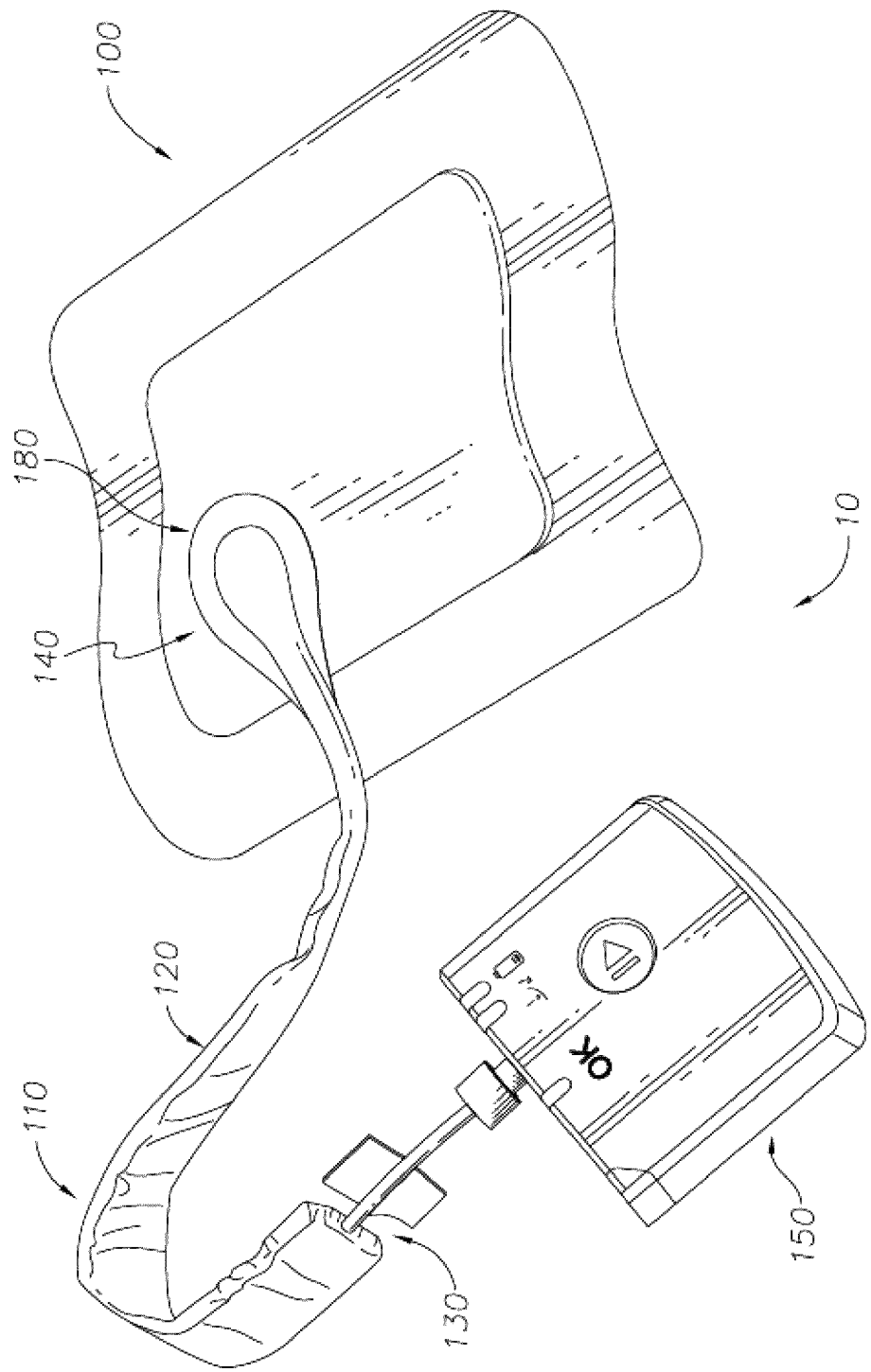
FIG. 2A illustrates an embodiment of a negative pressure wound treatment system employing a flexible fluidic connector and a wound dressing capable of absorbing and storing wound exudate.

Embodiments disclosed herein relate to apparatuses and methods for treating wounds and other tissues with therapeutic ultrasound, either with or without NPWT. The embodiments disclosed herein are not limited to treatment of a particular type of tissue or injury, instead the therapeutic ultrasound technologies disclosed herein are broadly applicable to any type of wounded or intact tissue that may benefit from therapeutic ultrasound. For example, the therapeutic ultrasound embodiments disclosed herein may be used to treat both internal and external wounds. Some embodiments disclosed herein relate to the use of therapeutic ultrasound delivered alone or in combination with a material layer (such as a dressing) configured to be used in the treatment of both intact and damaged human or animal tissue. The therapeutic ultrasound embodiments disclosed herein may be used with any of the signal parameters, such as intensity, timing, and frequency disclosed herein this section or elsewhere in the specification. Further details regarding the arrangement of a therapeutic ultrasound system within a dressing and optimization of the therapeutic ultrasound signal will be described in much greater detail later in the specification.

Further details regarding the impact of treatment with therapeutic ultrasound may be found in "Ultrasonic Stimulation of Mouse Skin Reverses the Healing Delays in Diabetes and Aging by Activation of Rac1," by Roper et al., "Therapeutic Ultrasound Bypasses Canonical Syndecan-4 Signaling to Activate Rac1" by Mahoney et al., and "Cytoplasmic interactions of syndecan-4 orchestrate adhesion receptor and growth factor receptor signaling" by Bass and Humphries. Further details regarding the cellular impact of therapeutic ultrasound may be found in "Induction of Adhesion-dependent Signals Using Low-Intensity Ultrasound" by Roper et al. Each of the aforementioned references are hereby incorporated by reference, attached as an appendix, and should be considered part of this specification.

The therapeutic ultrasound embodiments disclosed herein may be used in combination with clothing; for example, by incorporating an ultrasound transducer within layers of clothing. Non-limiting examples of clothing for use with therapeutic ultrasound disclosed herein include shirts, pants, trousers, dresses, undergarments, outer-garments, gloves, shoes, hats, and other suitable garments. The therapeutic ultrasound embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

The therapeutic ultrasound embodiments disclosed herein may be utilized in rehabilitation devices and treatments, including sports medicine. For example, the therapeutic ultrasound embodiments disclosed herein may be used in braces, sleeves, wraps, supports, and other suitable items.

The therapeutic ultrasound embodiments disclosed herein may be incorporated into implantable devices, such as implantable orthopedic implants, including flexible implants. Such embodiments may be configured to treat tissue surrounding the implant site. In some embodiments, an internal source may also provide power for such an implant.

Therapeutic ultrasound embodiments as disclosed herein may be incorporated into Ear, Nose, and Throat (ENT) applications. For example, such Therapeutic ultrasound embodiments may be utilized to treat the tissues of the passages of the ear, nose and throat.

In certain embodiments, the therapeutic ultrasound embodiments disclosed herein may be incorporated into an organ protection layer such as disclosed below. Such a therapeutic ultrasound incorporated organ protection layer may both protect the organ of interest and treat the underlying tissues and organs. As discussed above, the therapeutic ultrasound embodiments disclosed herein may be incorporated into treatments for wounds (disclosed in greater detail below) or in a variety of other applications. Non-limiting examples of additional applications for the therapeutic ultrasound embodiments disclosed herein include: treatment of intact skin, cardiovascular applications such as delivering therapeutic ultrasound to blood vessels, orthopedic applications such as delivering therapeutic ultrasound to intact and fractures bone and other skeletal tissues, neurophysiological applications such as delivering therapeutic ultrasound to the central and peripheral nervous system, and any other tissue, organ, system, or condition that may benefit from therapeutic ultrasound.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein)

wound with or without reduced pressure, including for example a source of negative pressure and wound dressing components and apparatuses.

The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer. The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

an absorbent layer for absorbing wound exudate and an obscuring element for at least partially obscuring a view of wound exudate absorbed by the absorbent layer in use.

The obscuring element may be partially translucent, and in certain embodiments the obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapour permeability of 500 g/m2/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is maybe suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene. The apertures may have an area from 0.005 to 0.32 mm2. The support layer may have a tensile strength from 0.05 to 0.06 Nm. The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in PCT patent publication WO201807872, filed on Oct. 24, 2017 with application number PCT/EP2017/077154, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on Dec. 12, 2016 with application number GB1621057.7; and Jun. 22, 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in PCT publication WO2011058311A1, filed with application number PCT/GB2010/002071, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in PCT Publication WO2005079718A1, filed Feb. 11 2005, as application PCT/GB2005/000517, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Therapy Dressings

In some embodiments, treatment of wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds. One of skill in the art will understand that the NPWT embodiments disclosed herein may be combined with any of the therapeutic ultrasound embodiments described herein to provide simultaneous or alternating therapeutic ultrasound and negative pressure.

It will be understood that embodiments of the present disclosure are generally applicable to use in topical negative pressure ("TNP") or negative pressure wound therapy (NPWT) systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing.

TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg The negative pressure range for some embodiments of the present disclosure can be approximately −80 mmHg, or between about −20 mmHg and −200 mmHg Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. Further, there may be additional effects on tissues in close proximity to the filler, for example, the tissue is under compression due to the reactive force of the elastic filler pressing on the tissue. Such compression may result in in local hypoxia due to occlusion of the blood vessels. In the wider peripheral tissue, this expansion may lead to blood vessel expansion. Further details are provided in "NPWT settings and dressing choices made easy" by Malmsjo and Borgquist, published in Wounds International in May 2010. For example, in a wound that is not at risk for ischemia, the increased and decreased blood flow caused by pressure from the wound dressing is likely advantageous for wound healing. The increase in blood flow may improve oxygen and nutrient supply to the tissue, and improve penetration of antibiotics and the removal of waste. Additionally, the reduction in blood flow may stimulate angiogenesis, thereby promoting granulation tissue formation.

Wound Healing

One of skill in the art will understand that the therapeutic ultrasound embodiments described herein are not merely applicable to situations involving wounds. Rather, such embodiments may be broadly applicable to situations that do not necessarily involve wounded tissues, such as treating intact tissues. Additionally, one of skill in the art will understand that the therapeutic ultrasound embodiments described herein may be used with any dressing embodiment described herein this section or elsewhere in the specification.

Wounds may be generally categorized as open or closed, often depending upon how the wound is caused. As described above, the techniques may be applied to both open and to closed wounds, depending on the particulars of the embodiment. Open wounds may be caused by a variety of events, including: incisions, lacerations, abrasions, punctures, pentetration, amputation, and other means. Closed wounds may be caused by damage to a blood vessel resulting in formation of a hematoma, and/or by internal injuries caused by crushing. Further, wounds may involve various layers of tissue, for example, shallower wounds may only involve the topmost layers of the skin, while deeper wounds may involve underlying subcutaneous tissue layers such as the hypodermis, including underlying connective tissues and fatty layers. In certain embodiments, wounds may even encompass underlying internal organs, deep beneath the skin. Certain wounds, such as those caused by pressure injuries, may start to occur within the deeper tissue layers without become evident on the surface of the skin until much later.

In addition to NPWT treatments described above, wounds may be treated by a wide variety of techniques and materials. For example, wounds may be treated by debridement to remove dead and/or necrotic tissue. Wounds may be treated with a with various type of dressings, including dry and wet dressings, chemically-impregnated dressings, foam dressing, hydrogel dressings, hydrocolloid dressings, film dressings, and other suitable dressings. Wounds may further be treated with bioactive molecules such as antimicrobials, growth factors, anti-inflammatories, analgesics and other suitable treatments. Such treatments may be incorporated into the aforementioned dressings.

Further details regarding wounds and wound treatment, in particular wounds caused by pressure injuries may be found in the article "Pressure Injuries (Pressure Ulcers) and Wound Care" by Kirman et al, published in Medscape March 2017. For example, the most common candidates for pressure ulcers include: elderly persons, persons who are chronically ill (such as those with cancer, stroke, or diabetes), persons who are immobile (e.g, as a consequence of fracture, arthritis, or pain), persons who are weak or debilitated, patients with altered mental status (e.g., from the effects of narcotics, anesthesia, or coma), and/or persons with decreased sensation or paralysis. Potential secondary factors include: illness or debilitation that increases pressure ulcer formation, fever (increases metabolic demands), predisposing ischemia, diaphoresis which promotes skin maceration, incontinence which causes skin irritation and contamination, edema, jaundice, pruritus, and xerosis (dry skin). Additionally, prevention of pressure ulcer injuries may include: scheduled body turning, appropriate bed positioning, protection of bony prominences, skin care, control of spascity and prevention of contractures, use of support surfaces/specialty beds, nutritional support, and maintenance of current levels of activity, mobility and range of motion.

Negative Pressure Wound Therapy Systems

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a target or desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Self-Contained Wound Dressing

Figure 2B:
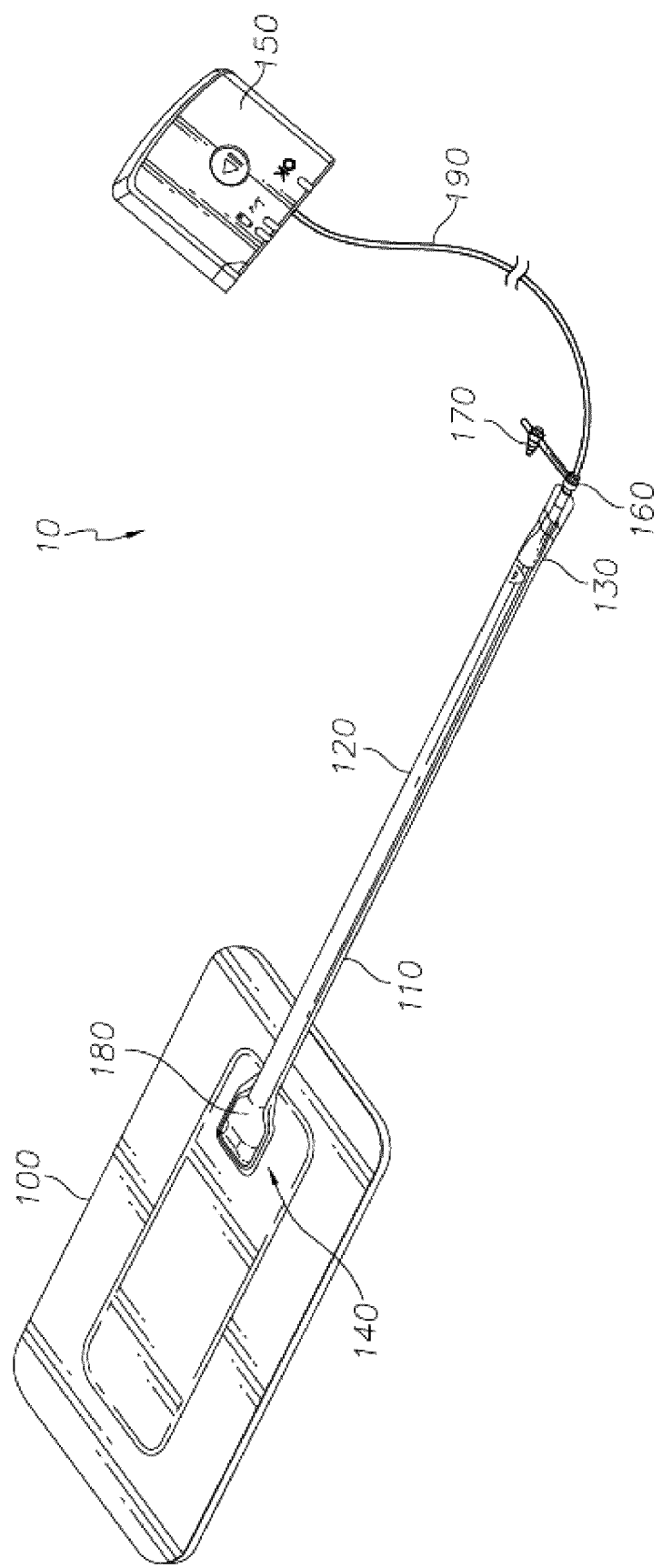
FIG. 2B illustrates an embodiment of a negative pressure wound treatment system employing a flexible fluidic connector and a wound dressing capable of absorbing and storing wound exudate.

In certain embodiments, NPWT may be applied from a suitable source such as a pump, to a wound through a self-contained wound dressing, such as a PICO™ wound dressing, as sold by Smith & Nephew. FIGS. 2A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 3A:
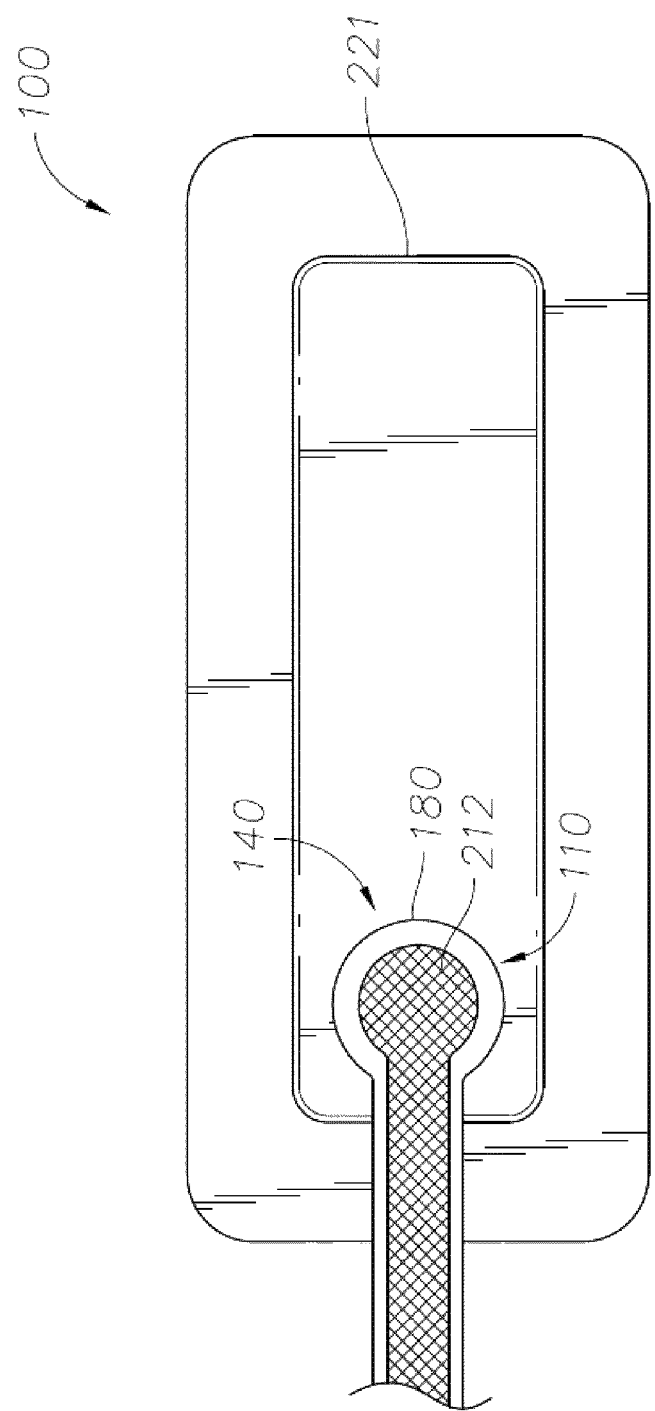
FIG. 3A illustrates an embodiment of a negative pressure wound treatment system employing a flexible fluidic connector and a wound dressing capable of absorbing and storing wound exudate.

As shown in FIG. 3A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 3B:
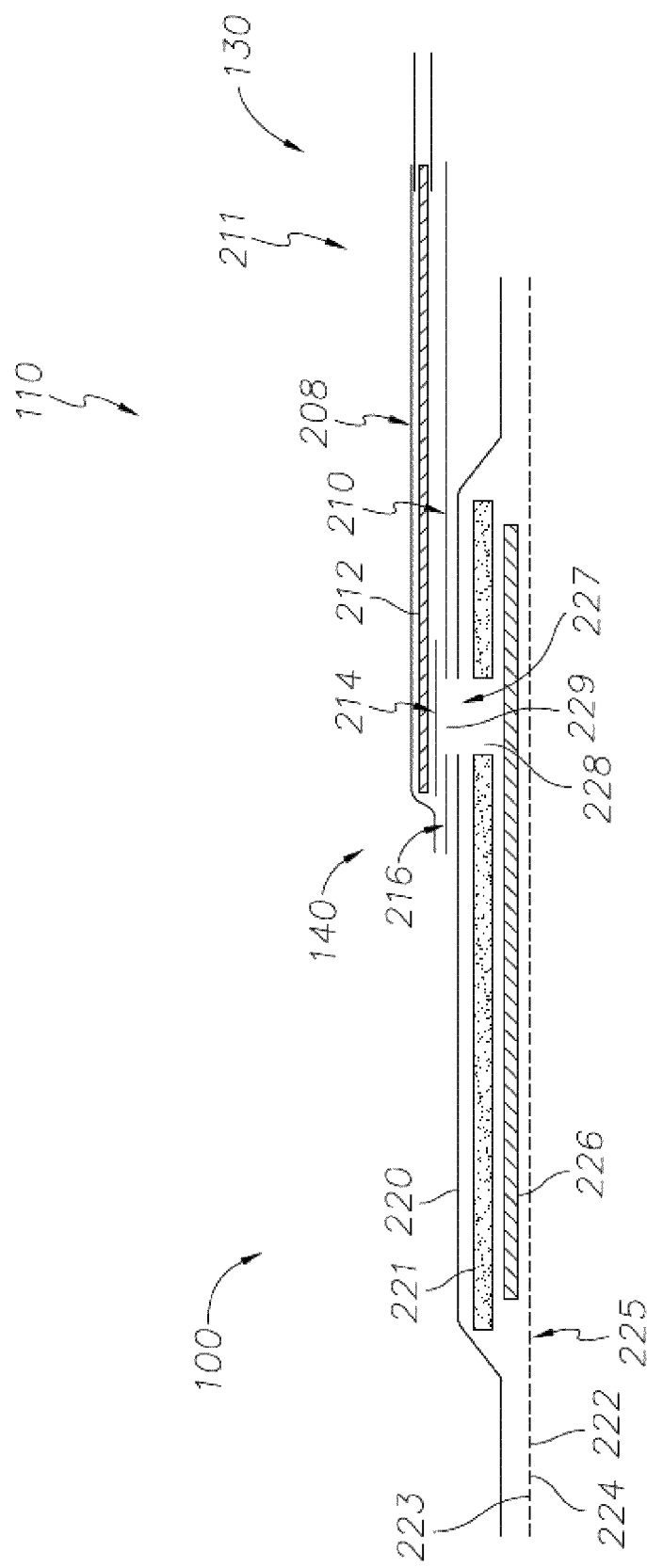
FIG. 3B illustrates a cross section of an embodiment of a fluidic connector connected to a wound dressing.

FIG. 3B illustrates a cross-section through a wound dressing 100 similar to the wound dressing 10 as shown in FIG. 2B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 3B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 3B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 3B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial bather) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 6A-6B, the absorbent layer 221 may define a smaller perimeter than that of the backing layer 220, such that a boundary or border region is defined between the edge of the absorbent layer 221 and the edge of the backing layer 220.

As shown in FIG. 3B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 3A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 2A-2B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. Pat. No. 8,801,685, which is incorporated by reference herein in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the present disclosure, filter element 214 comprises a support layer and an acrylic co-polymer membrane formed on the support layer. Preferably the wound dressing 100 according to certain embodiments of the present disclosure uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 100 may comprise spacer elements 215 in conjunction with the fluidic connector 110 and the filter 214. With the addition of such spacer elements 215 the fluidic connector 110 and filter 214 may be supported out of direct contact with the absorbent layer 220 and/or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. A fluidic connector can be bonded above the hole, the fluid connector comprising a liquid-impermeable, gas-permeable semi-permeable membrane (SPM) or filter that overlies the aforementioned apertures.

Treatment of Abdominal Wounds

Figure 4:
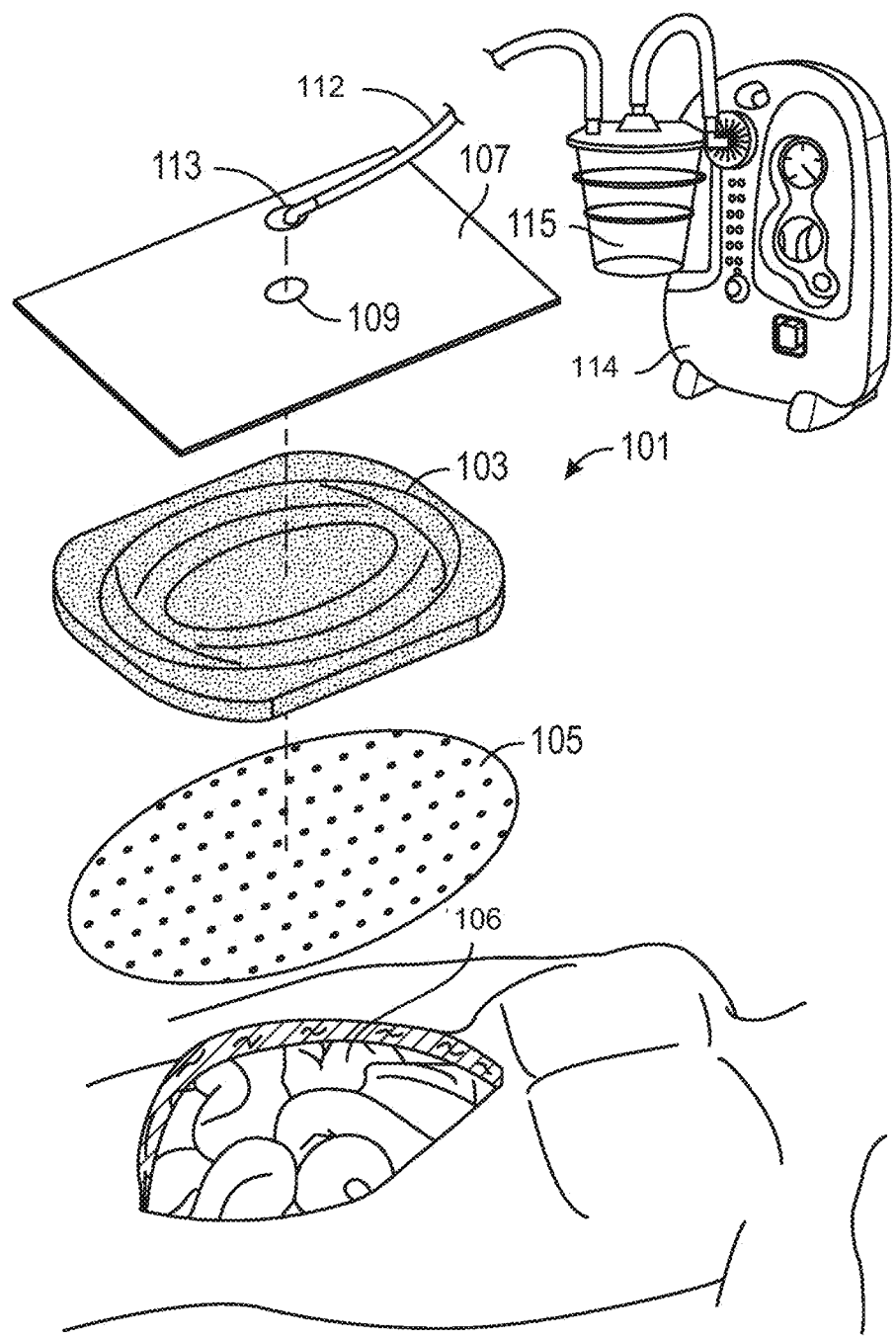
FIG. 4 illustrates an embodiment of a negative pressure wound therapy system.

Turning to FIG. 4, treatment of other wound types, such as larger abdominal wounds, with negative pressure in certain embodiments uses a negative pressure treatment system 101 as illustrated schematically here. In this embodiment, a wound site 106, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 106 can be beneficial to a patient.

Accordingly, certain embodiments provide for a wound contact layer 105 to be placed over the wound site 106. The wound contact layer can also be referred to as an organ protection layer and/or a tissue protection layer. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 106 or the transmittal of negative pressure to the wound site 106. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound site 106. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound site 106. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Therapeutic Ultrasound Wound Treatment Apparatuses

Throughout the specification and in particular within the paragraphs below, reference may be made to ultrasound (US), ultrasonic energy, ultrasound energy, and/or high frequency vibrational energy. One of skill in the art will understand that high frequency vibrational energy is often used interchangeably with ultrasound or ultrasonic energy by those of skill in the art.

Cellular behavior within multi-cellular organisms is dictated by interactions with the extracellular matrix, the materials and structures outside of a cell that make a grouping of cells into a tissue. Cellular engagement with the extracellular matrix can result in a number of consequences, such as regulation of cell migration and proliferation, secretion, and differentiation. The interaction of cells with the surrounding extracellular matrix is a critical component of wound healing. It is thought that selective application of ultrasound to a wound or other tissue can alter cellular behavior, potentially improving and speeding up the healing process. Fibroblasts are highly prevalent in the human dermis and play a critical role in wound healing. Fibroblasts assist in wound healing by forming granulation tissue and generating new extra-cellular matrix components, such as the formation of collagen at a wound site. However, like many cells, fibroblasts can be impaired by various disease states such as diabetes and other patient comorbidities. Under certain stressful conditions, fibroblasts may develop a stress-induced premature senescence phenotype. In chronic wounds, populations of greater than 15% senescent fibroblasts has been described as a threshold beyond which healing is impaired.

Figure 5:
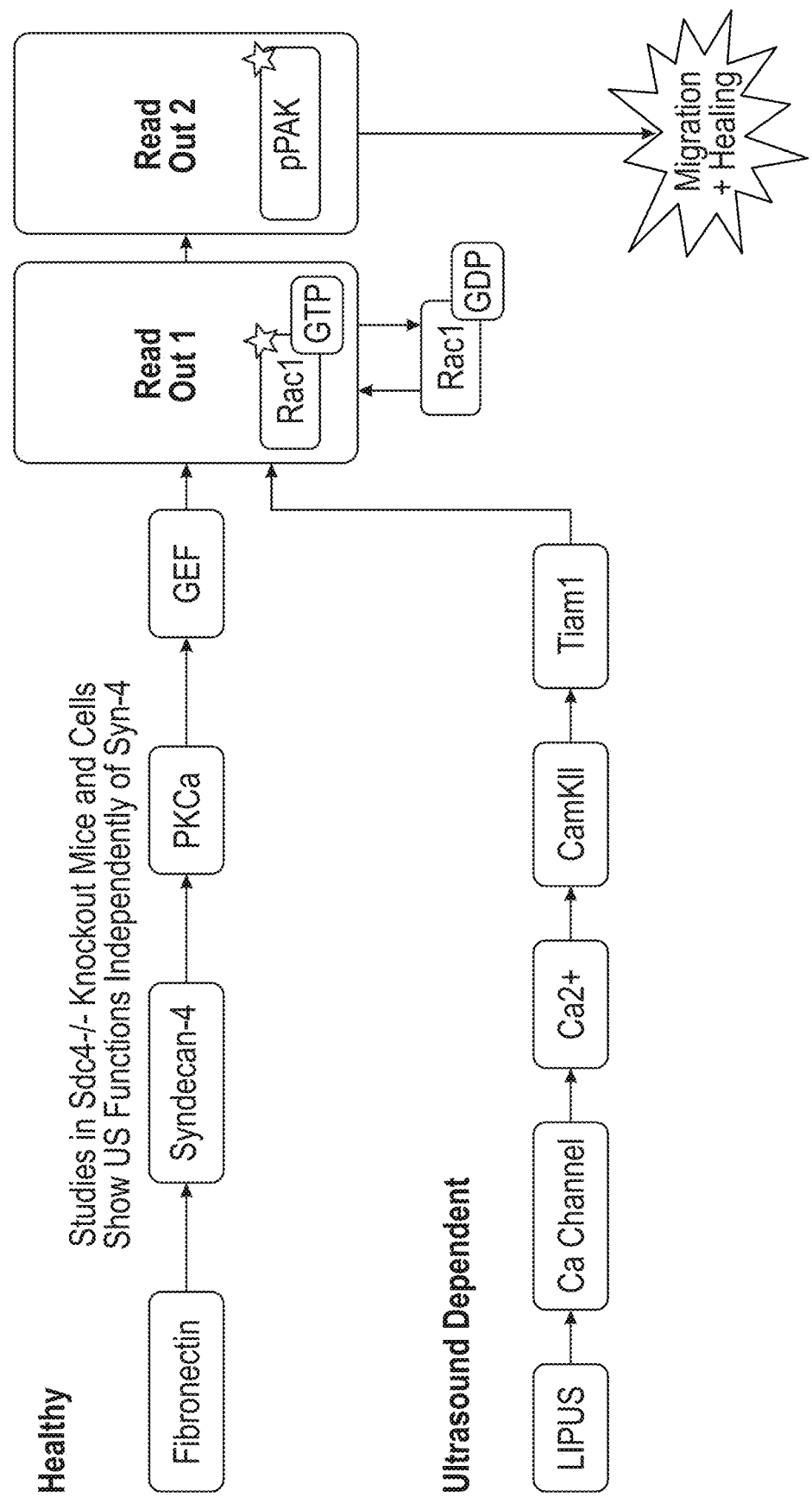
FIG. 5 illustrates a schematic of an embodiment of an ultrasound dependent signaling pathway.

FIG. 5 depicts an embodiment of a possible mechanism by which ultrasound may activate an alternative calcium channel dependent pathway resulting in increased Rac1 signaling. Rac1 is a common signaling protein found in human cells, known to increase cellular events related to healing such as glucose uptake, cell growth, cytoskeletal reorganization, antimicrobial cytotoxicity, and the activation of protein kinases. As shown in FIG. 5, Rac1 interacts with serine/threonine-protein kinase (PAK) in a Guanosine-5'-triphosphate (GTP) mediated interaction to induce migration and healing. In brief, in healthy fibroblasts, a fibronectin-mediated pathway results in increased cell migration and healing. When this pathway is disrupted via stressors, such as described above, then cellular migration and healing are impaired. However, in instances where the fibronectin-medicated pathway is disrupted, an alternative ultrasound-dependent healing pathway may be activated. By stimulating this ultrasound-dependent pathway, it is thought that therapeutic ultrasound improves wound healing. Further details regarding the signal parameters for optimizing the therapeutic ultrasound signal for maximal wound healing are detailed later in the specification, particularly in FIGS. 15-21.

Figure 6:
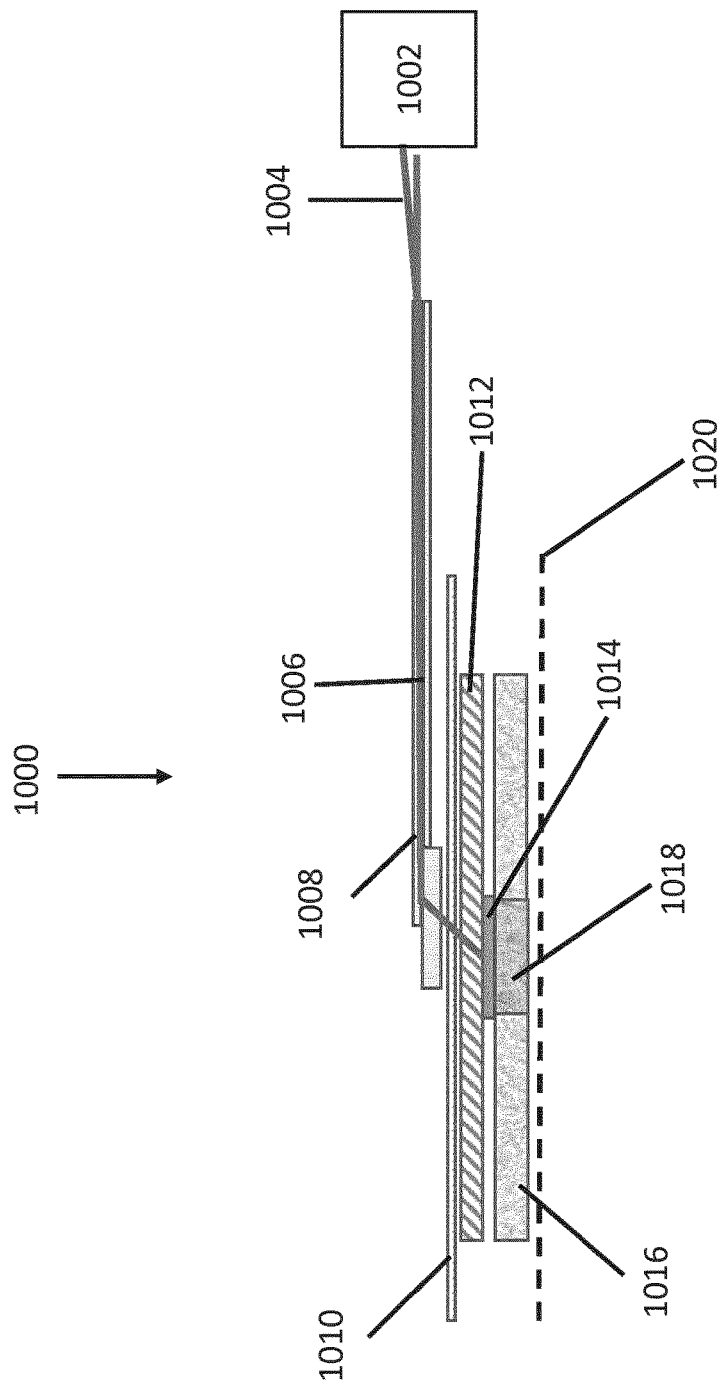
FIG. 6 illustrates an embodiment of a therapeutic ultrasound wound treatment apparatus.

FIG. 6 depicts an embodiment of a therapeutic ultrasound wound treatment apparatus 1000 for use in treating a wound, similar to the dressings described above in FIGS. 1-3B. In certain embodiments, a suitable signal may be delivered to the dressing from an ultrasonic frequency electrical signal generator 1002, via wires 1004. One of skill in the art will understand that the signal may have any parameters such as timing, intensity, and frequency disclosed herein this section or elsewhere in the specification, particularly the parameters disclosed later in the specification with respect to FIGS. 13-17. The ultrasonic frequency electrical signal generator may be of any suitable type, for example, the EXOGEN generator manufactured by Bioventus. The wires may be contained within a channel 1006 contained within a port 1008, such as the soft port described above in relation to FIGS. 1-3B. In certain embodiments, the channel 1006 may have 2 layers of spacer to provide space for the wires to pass. The port may be connected to a cover layer 1010, which may be adhered to the port via a constructional adhesive. The cover layer can overlay an absorbent layer 1012, the absorbent layer constructed from any material disclosed herein this section or elsewhere in the specification, for example a cellulose material with embedded superabsorbent particles. An ultrasonic transducer 1014 may be located beneath the absorbent layer. The ultrasonic transducer may be of any suitable type, such as a piezoelectric transducer, a capacitive transducer, and/or any suitable transducer such as those described in PCT. Pub. No. WO1999/056829, PCT. Pub. No. WO 1999/048621, and U.S. Pat. No. 5,904,659, all of which are hereby incorporated by reference. Once the ultrasonic transducer is stimulated by a suitable electrical signal from the signal generator 1002, the transducer will emit a therapeutic ultrasonic signal. The therapeutic signal provided by the transducer may be highly variable in terms of timing of pulsation, frequency, and intensity. Further details regarding the therapeutic signal are provided below. In some embodiments, the therapeutic ultrasound wound treatment apparatuses disclosed herein may comprise about: one, two, three, four, five, ten, fifteen, 25, 50, 75, 100, 150, 200, 300 or more ultrasonic transducers. In certain embodiments, the ultrasonic transducers may be organized into a grid, such as a grid contained within a flexible substrate.

In certain embodiments, the ultrasound signal should be delivered to the wounded surface with sufficient intensity to stimulate healing. Therefore, it is desirable that a delivery pathway be available for the therapeutic ultrasound to be effectively transmitted to the surface. Such a delivery pathway may be provided by a delivery layer 1016 comprising a transmission portion 1018. In certain embodiments, the delivery layer may comprise foam surrounding the transmission portion 1018. For example, the delivery layer may be constructed from a polyurethane foam or any suitable material such as disclosed herein this section or elsewhere in the specification. In some embodiments, the delivery layer may comprise one, two, three, four, five, ten, fifteen, or more transmission portions. The transmission portions may have any suitable shape, such as a column, a pillar, a cuboid, or a rectangular parallelepiped. In embodiments the transmission portion may be in the form of a strip or a series of layered strips adjacent to a transducer. Any shape may be suitable for the transmission portion, provided that there is a continuous transmission portion "line-of-sight" between the transducer and the wounded tissue. Ultrasound transmission is sensitive to the medium used for transmission, therefore without a path to the wound of transmission material, the ultrasound may not reach the wound.

The transmission portion 2018 may be constructed from any suitable material for conveying high frequency vibrational energy, such as a silicone gel, a silicone adhesive (for example 2111 silicone adhesive), Cica Care silicone gel, Durafiber that may be wetted out, or ultrasound connection gel surrounded by a film bubble. In certain embodiments, a series of silicone strands may be embedded in the delivery layer, thereby allowing for multiple ultrasound pathways.

A wound contact layer may be positioned beneath the delivery layer. The wound contact layer may be constructed from any suitable material such as disclosed herein this section or elsewhere in the specification. For example, the wound contact layer may be constructed from polyurethane alone or polyurethane coated with a silicone adhesive on the bottom, top, or both the bottom or the top of the wound contact layer. In some embodiments, the wound contact layer itself may be replaced with a silicone adhesive layer. The wound contact layer may be constructed as a film layer coated in an acrylic constructional adhesive.

One of skill in the art will understand that in embodiments the wound contact layer and the delivery layer, outside of the transmission portion, may be porous thereby allowing wound exudate to pass through the wound contact layer and the delivery layer, to be absorbed within the absorbent layer. In some embodiments, negative pressure may also be applied to the wound treatment apparatuses of FIGS. 6-11, thereby allowing for the simultaneous application of therapeutic ultrasound and NPWT. In embodiments, NPWT may be applied in an alternating fashion with therapeutic ultrasound. Advantageously, application of negative pressure may serve to draw the dressing and/or substrate downward toward the wound, thereby bringing the transducers and/or transmission medium(s) directly into contact with tissue and/or exudate. Bringing the dressing or substrate into direct contact with tissue and/or exudate advantageously may reduce signal lost through transmission through air.

One of skill in the art will further understand that the positioning of the various layers and components as described in FIG. 6 is for illustrative purposes, and the ultrasound transducer may be positioned in various locations within the dressing. For example, the ultrasound transducer may be placed directly against the wound contact layer, on the sides of the dressing, near the center of the dressing, off-center within the dressing, or any other suitable position.

Figure 7:
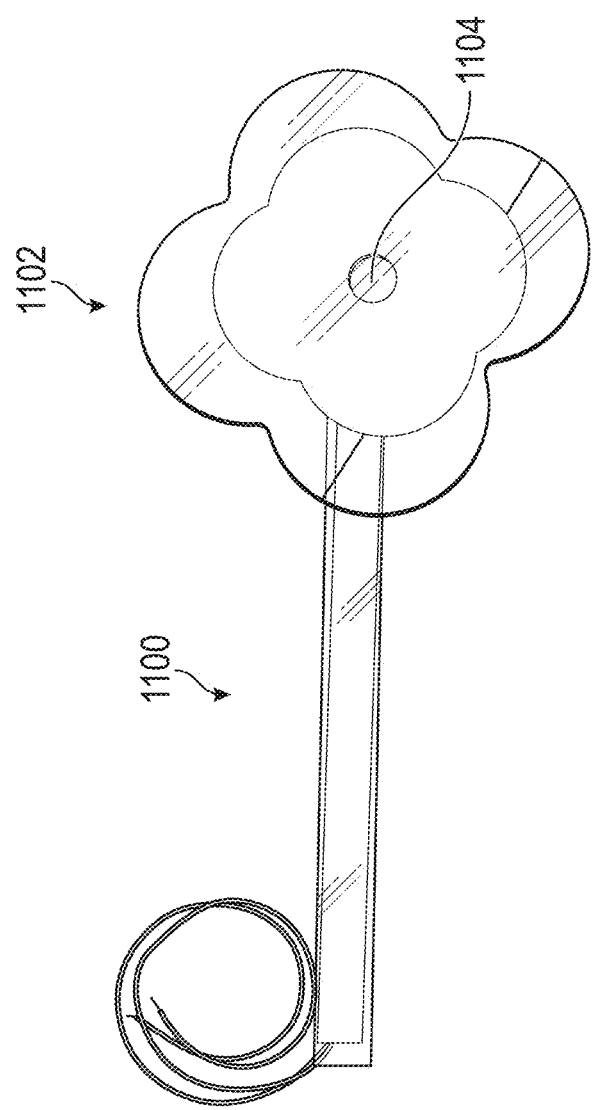
FIG. 7 is a photograph of an embodiment of a therapeutic ultrasound wound treatment apparatus.

FIG. 7 depicts a bottom view of an embodiment of a lobed therapeutic ultrasound wound treatment apparatus 1100, similar to the apparatus of FIG. 6. Here the shape of the apparatus may be in the form of a four-lobed dressing 1102. However, in certain embodiments, the dressing may be oval shaped, rectangular, single-lobed, double-lobed, triple-lobed, or comprise five or more lobes. The dressing may further be shaped according to any shape or size disclosed herein this section or elsewhere in the specification. Here, as in FIG. 6, the transmission portion 1104 may be centrally located within the dressing portion of the apparatus.

Figure 8A:
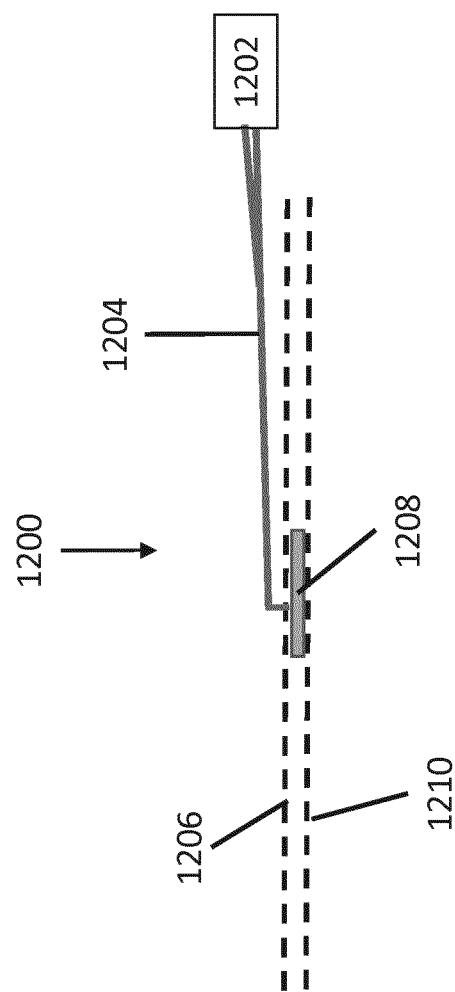
FIG. 8A illustrates an embodiment of a therapeutic ultrasound wound treatment apparatus.
Figure 8B:
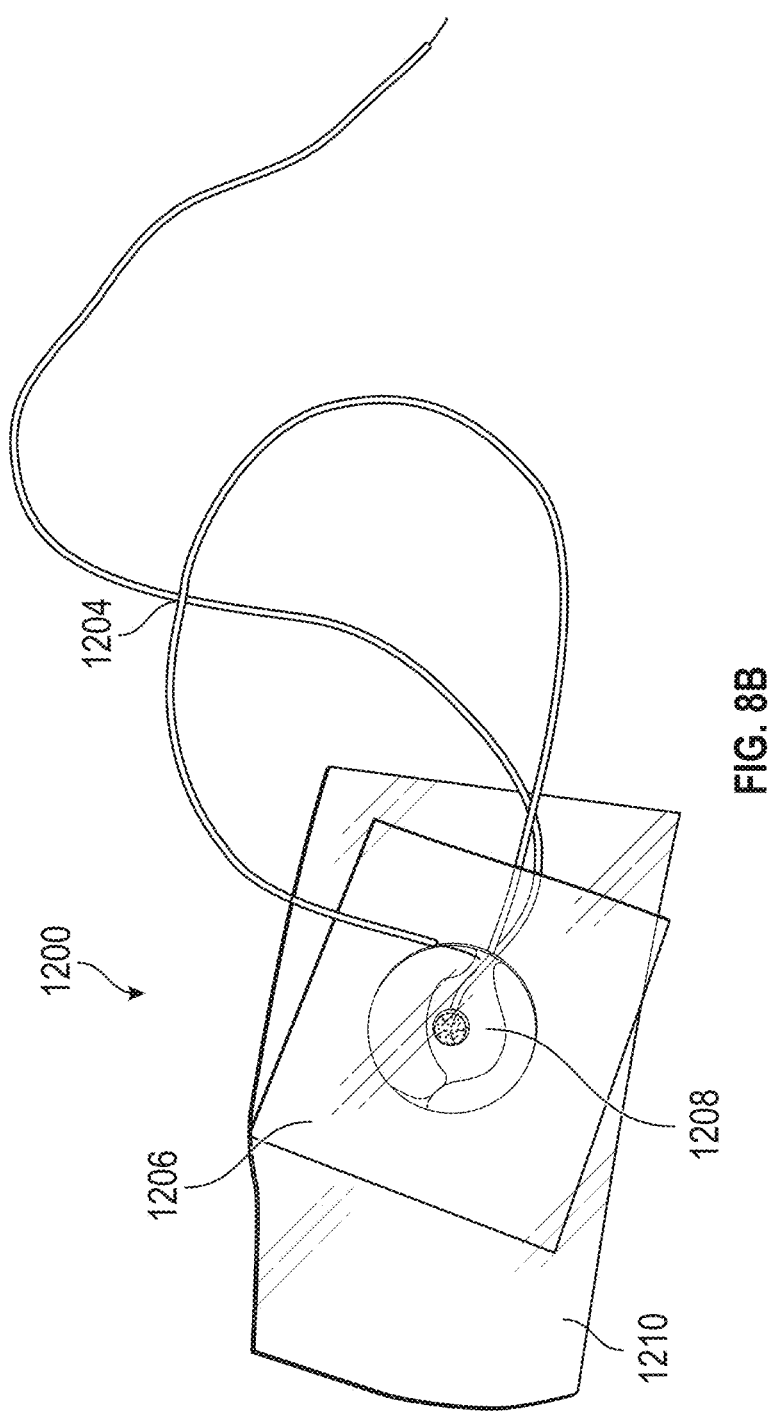

FIG. 8A depicts an embodiment of a therapeutic ultrasound wound treatment apparatus 1200 with some similarities to the embodiments of FIGS. 6 and 7. An ultrasonic frequency electrical signal generator 1202 connects to a transducer 1208 via wires 1204. However, here the transducer 1208 may be placed directly over the wound contact layer 1120. In embodiments, the wound contact member may be any material disclosed herein, such as silicone. The transducer may then be encapsulated by cover layer 1206. FIG. 8B is a photograph of the embodiment of FIG. 8A, shown from the top, while FIG. 8C is a photograph of the embodiment of FIG. 8A, shown from the bottom. Wires 1204, cover layer 1206, transducer 1208, and wound contact layer 1210 are shown.

Figure 9:
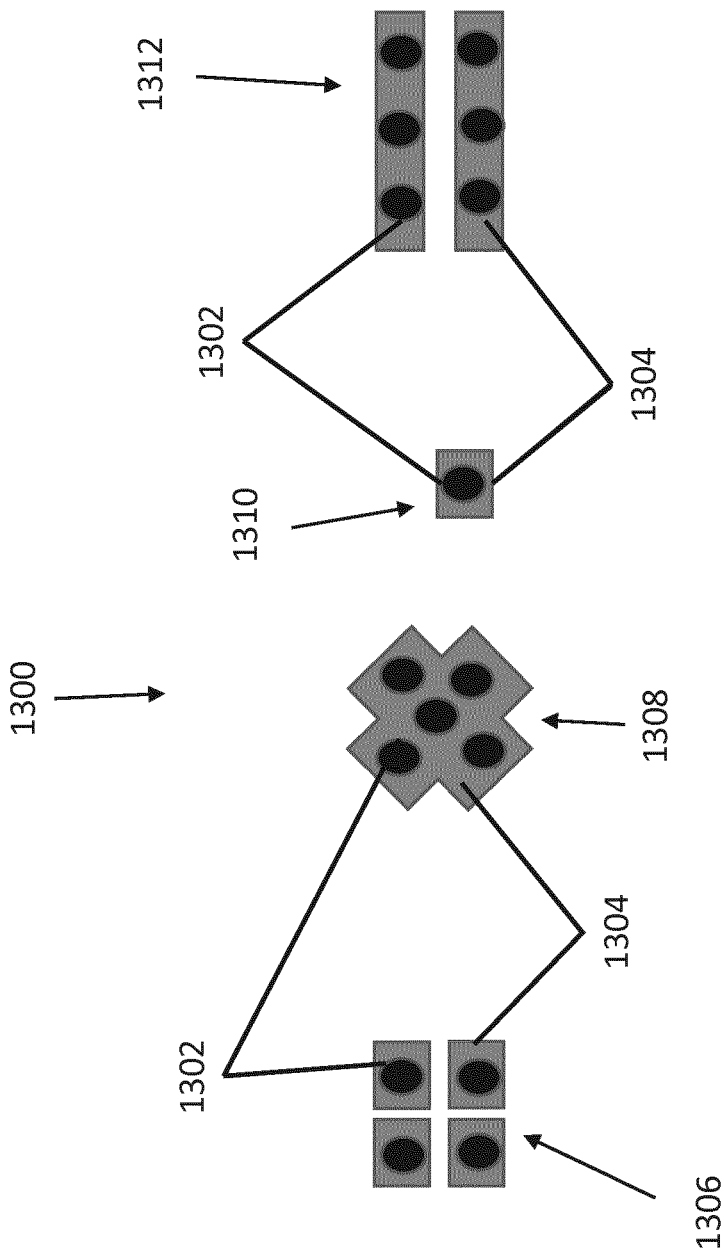
FIG. 9 illustrates embodiments of arrangements of ultrasonic transducers.

FIG. 9 depicts various embodiments of arrangements 1300 of transducers 1302 and transmission materials 1304 in strip form, such as within an ultrasound wound treatment apparatus as depicted in FIGS. 7-8C. For example, the transducers and transmission materials can be organized into a square formation with 4 transducers 1306. Alternatively, the transducers can be organized in a cross formation, with 5 transducers 1308. In embodiments, there may be only a single transducer 1310 or rows of transducers 1312 positioned on a single strip or multiple strips of transmission material. In embodiments, the ultrasonic transducers may be arranged in a circular pattern, a spiral pattern, an array, or any suitable arrangement.

Figure 10A:
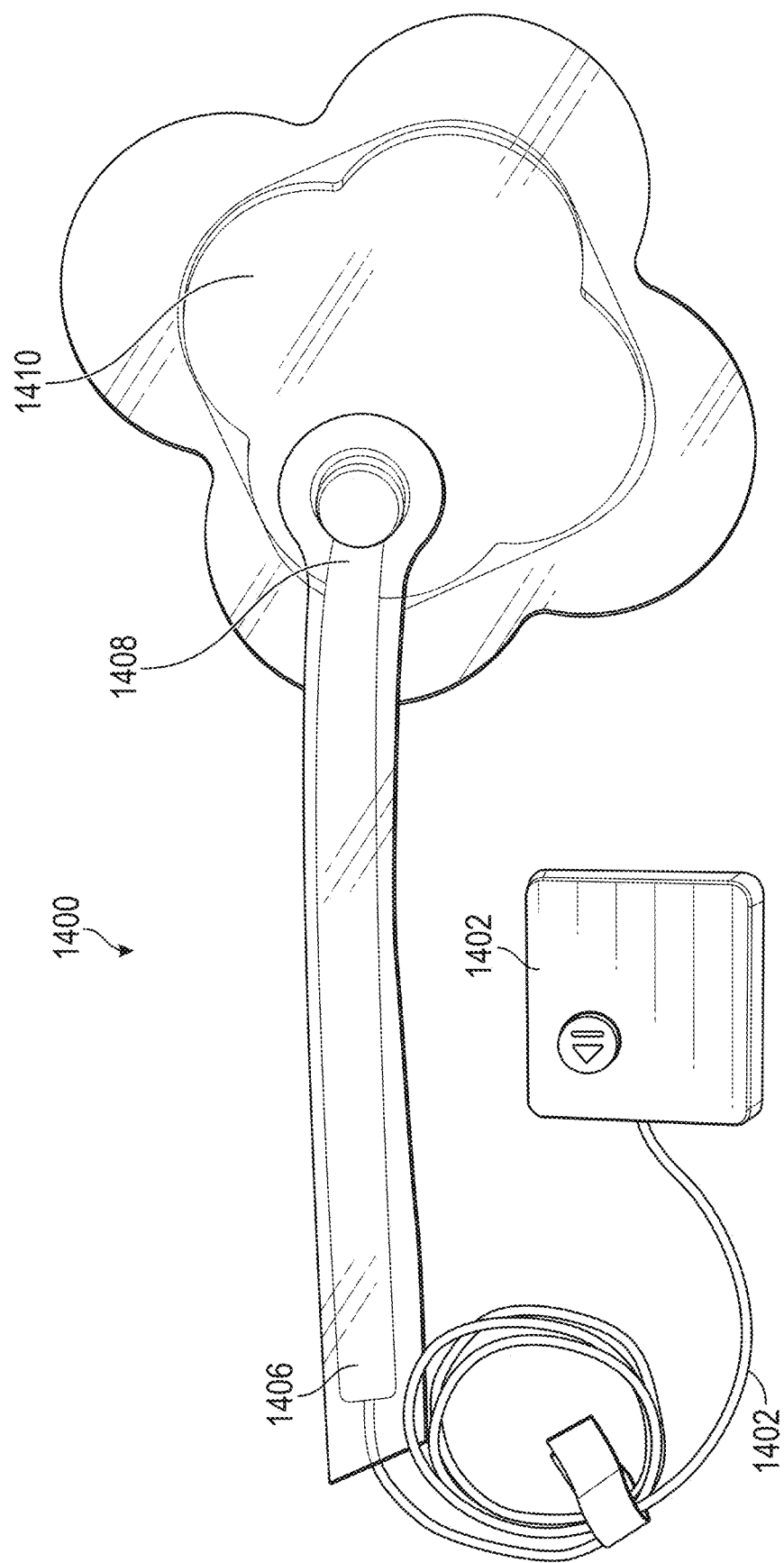
FIGS. 10A-B are photographs of therapeutic ultrasound wound treatment apparatuses.
Figure 10B:
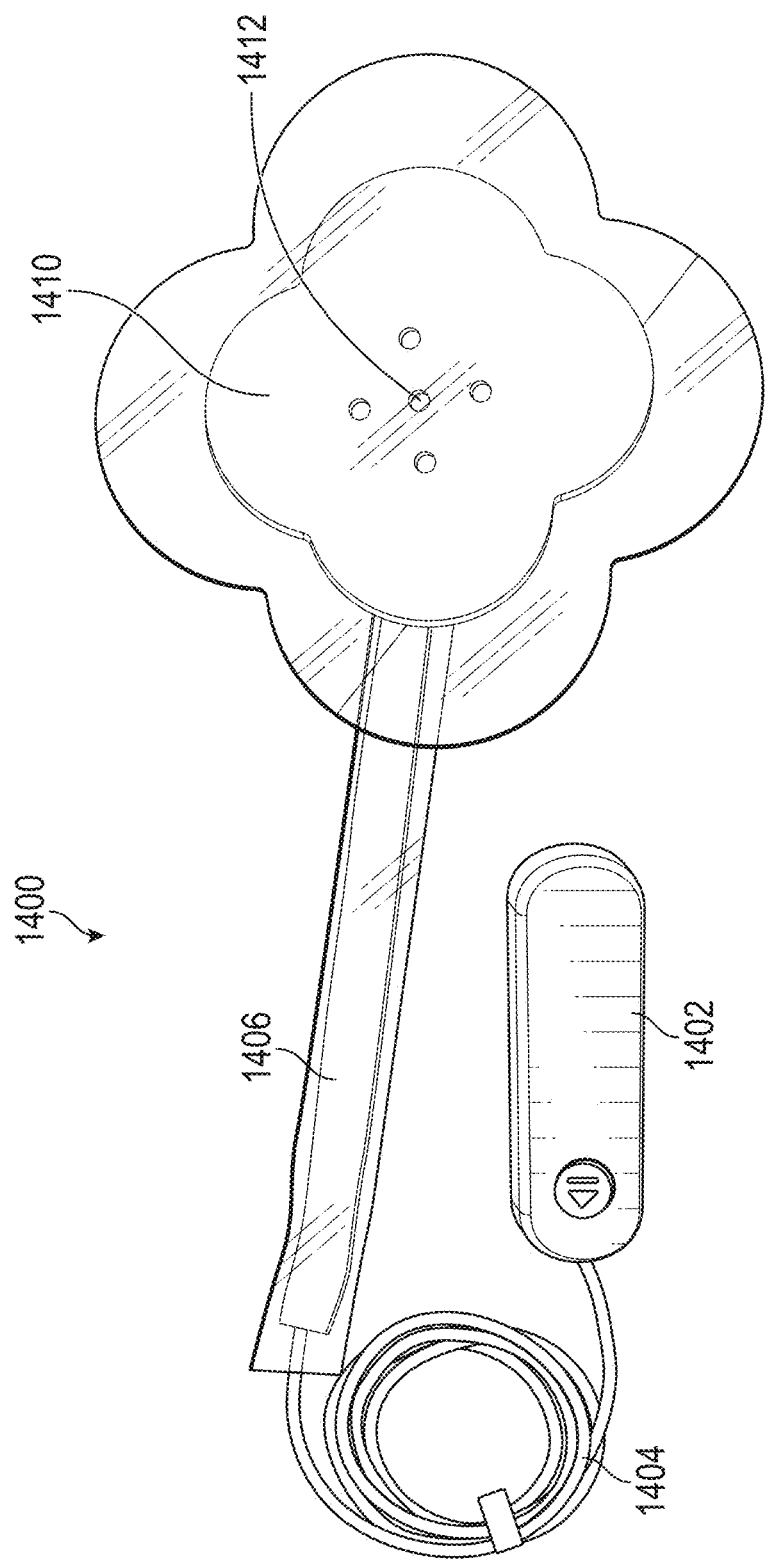

FIGS. 10A-10B depict an embodiment of a therapeutic ultrasound delivery apparatus 1400 that may be configured to deliver ultrasound alone or deliver both ultrasound and negative pressure. Treatment module 1402 may be an ultrasonic frequency electrical signal generator or a negative pressure generating pump, or contain both an ultrasonic frequency electrical signal generator and a pump. Both wires and tubing 1404 may extend from treatment module 1402 through channel 1406 to port 1408 and absorbent dressing 1410. Dressing 1410 may comprise any construction described herein this section or elsewhere in the specification, particularly as relate to FIGS. 2A-3B. On the underside of dressing 1410, there may be a plurality of transmission portions 1412, for example five, and a plurality of ultrasonic transducers positioned within the dressing (not shown). The number of transmission portions and ultrasonic transducers may be of any number disclosed herein this section or elsewhere in the specification.

Figure 11:
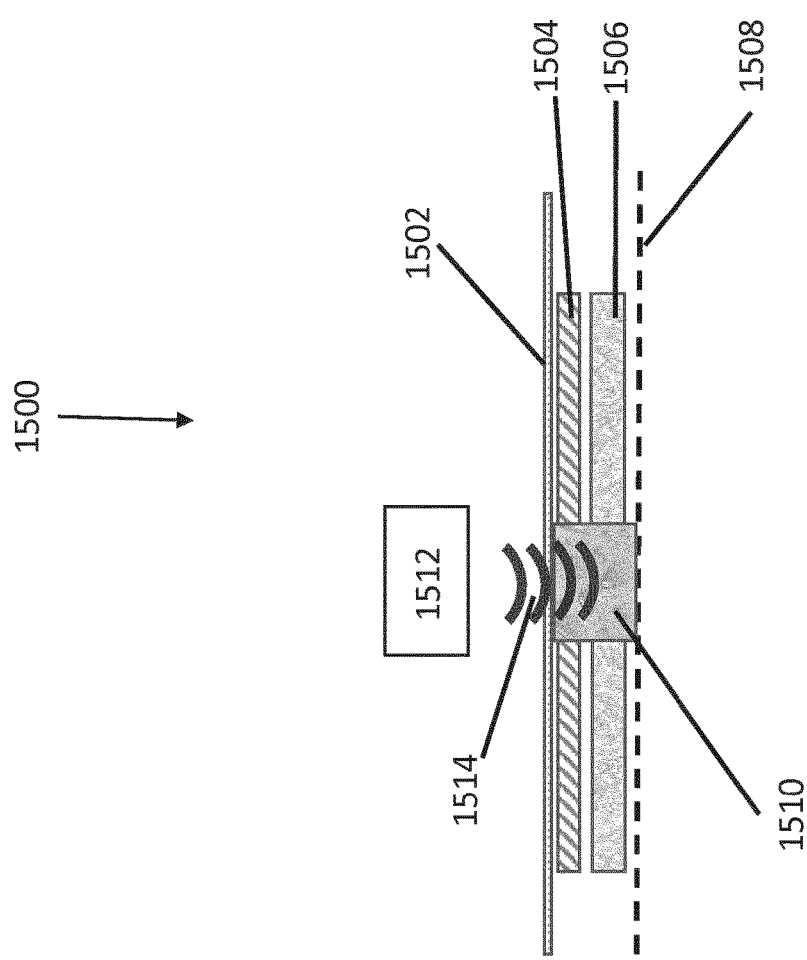
FIG. 11 illustrates an embodiment of a dressing that may be used with ultrasound.

FIG. 11 depicts an embodiment of a therapeutic ultrasound delivery apparatus 1500 similar to the apparatuses of FIGS. 6, 7, 10A, and 10B and the dressings described above in relation to FIGS. 2-3. Here, the apparatus includes a cover layer 1502, an absorbent layer 1504, a delivery lay 1506, and a wound contact layer 1508. However, a transmission portion extends from the wound contact layer through the delivery layer and the absorbent layer to the cover layer 1502. The positioning of the transmission portion now allows an ultrasound pathway from the top of the dressing to the bottom of the dressing. Therefore an ultrasonic transducer 1512 may be positioned over the transmission portion 1510 and deliver therapeutic ultrasound through the dressing 1500. In some embodiments, the transducer may be mounted to the top of the dressing or may be an external device that can be applied and removed at will.

Figure 12:
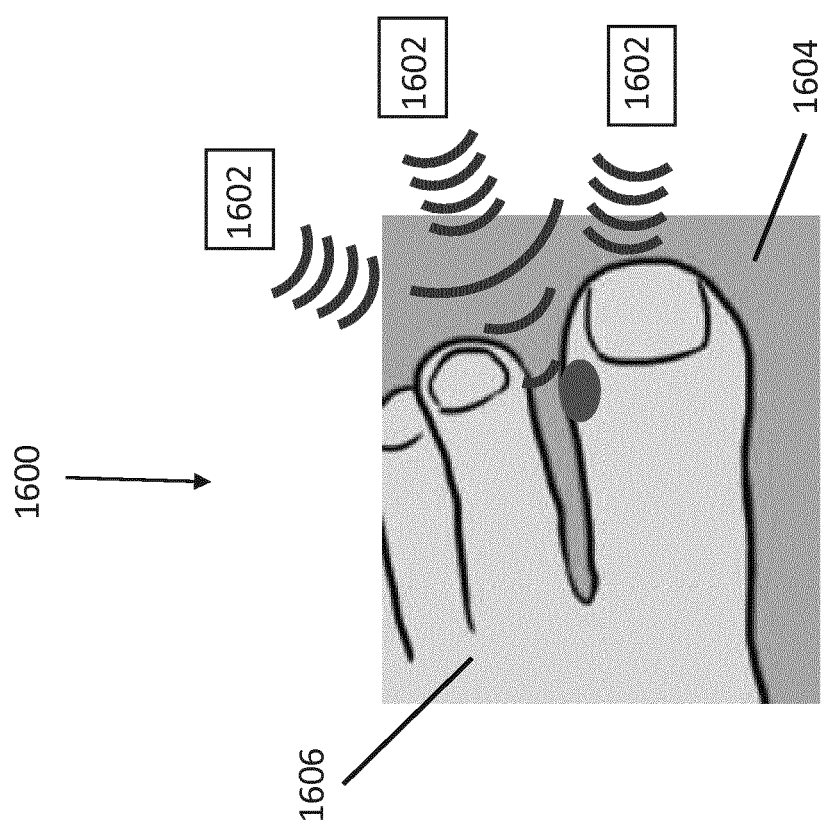
FIG. 12 illustrates an embodiment of an ultrasonic foot bath.

FIG. 12 depicts an embodiment of a diabetic foot ulcer treatment bath 1600. A plurality of ultrasonic transducers 1602 may be positioned around a container filled with liquid 1604, configured to receive a human foot 1606. Since liquid acts as a medium for transmission of ultrasound 1606, ultrasound may be delivered to the foot from multiple angles from the plurality of transducers. Due to the contours of the foot, it is particularly difficult to treat foot wounds, therefore by creating a bath of ultrasound, it is possible to ensure that even the most difficult to reach wound areas are bathed in ultrasound.

Therapeutic Ultrasound Signal

As described above, fibroblasts may be sensitive to application of ultrasound, increasing migration and healing in response to ultrasound signal delivery within a wound. However, the parameters of an ultrasound signal can be modified in a number of ways, such as by altering the voltage, frequency, or other parameters.

In certain embodiments, the frequency of the therapeutic ultrasound signal may range from: about 0.1-10 MHz, about 0.5-9 MHz, about 1-8 MHz, about 1.5-7 MHz, about 2-6 MHz, 3-5 MHz, or about 4 MHz. In some embodiments the frequency may be about 0.5 MHz, about 1 MHz, about 1.5 MHz, about 2 MHz, about 2.5 MHz, about 3 MHz, about 3.5 MHz, about 4.0 MHz, about 4.5 MHz, about 5 MHz, or greater than about 5 MHz.

In some embodiments, the acoustic power (power per unit area) of the therapeutic ultrasound signal may range from about 0.1 mW/cm$^2$ to 500 mW/cm$^2$, about 1 mW/cm$^2$ to 400 mW/cm$^2$, about 10 mW/cm$^2$ to 300 mW/cm$^2$, about 20 mW/cm$^2$ to 200 mW/cm$^2$, 30 to 100 mW/cm$^2$, or about 40-50 mW/cm$^2$. The acoustic power may also be about 1.5 mW/cm$^2$ to 60 mW/cm$^2$ or greater than 500 mW/cm$^2$. In certain embodiments, the acoustic power may be about 0.5 mW/cm$^2$, about 2 mW/cm$^2$, about 3 mW/cm$^2$, such as about 3.1 mW/cm$^2$, about 4 mW/cm$^2$ such as 4.2 mW/cm$^2$, about 5 mW/cm$^2$, about 15 mW/cm$^2$, about 25 mW/cm$^2$, about 30 mW/cm$^2$ such as 30.1 mW/cm$^2$, about 35 mW/cm$^2$, about 50 mW/cm$^2$, about 75 mW/cm$^2$, or about 125 mW/cm$^2$. In embodiments the acoustic power may range from about 2 mW/cm$^2$ to 6 mW/cm$^2$ or from about 25 mW/cm$^2$ to 35 mW/cm$^2$. One of skill in the art will appreciate that the relationship between the voltage input and the acoustic power output may vary for a particular transducer/ultrasonic frequency electrical signal generator combination versus a different transducer/ultrasonic frequency electrical signal generator combination.

Figure 13A:
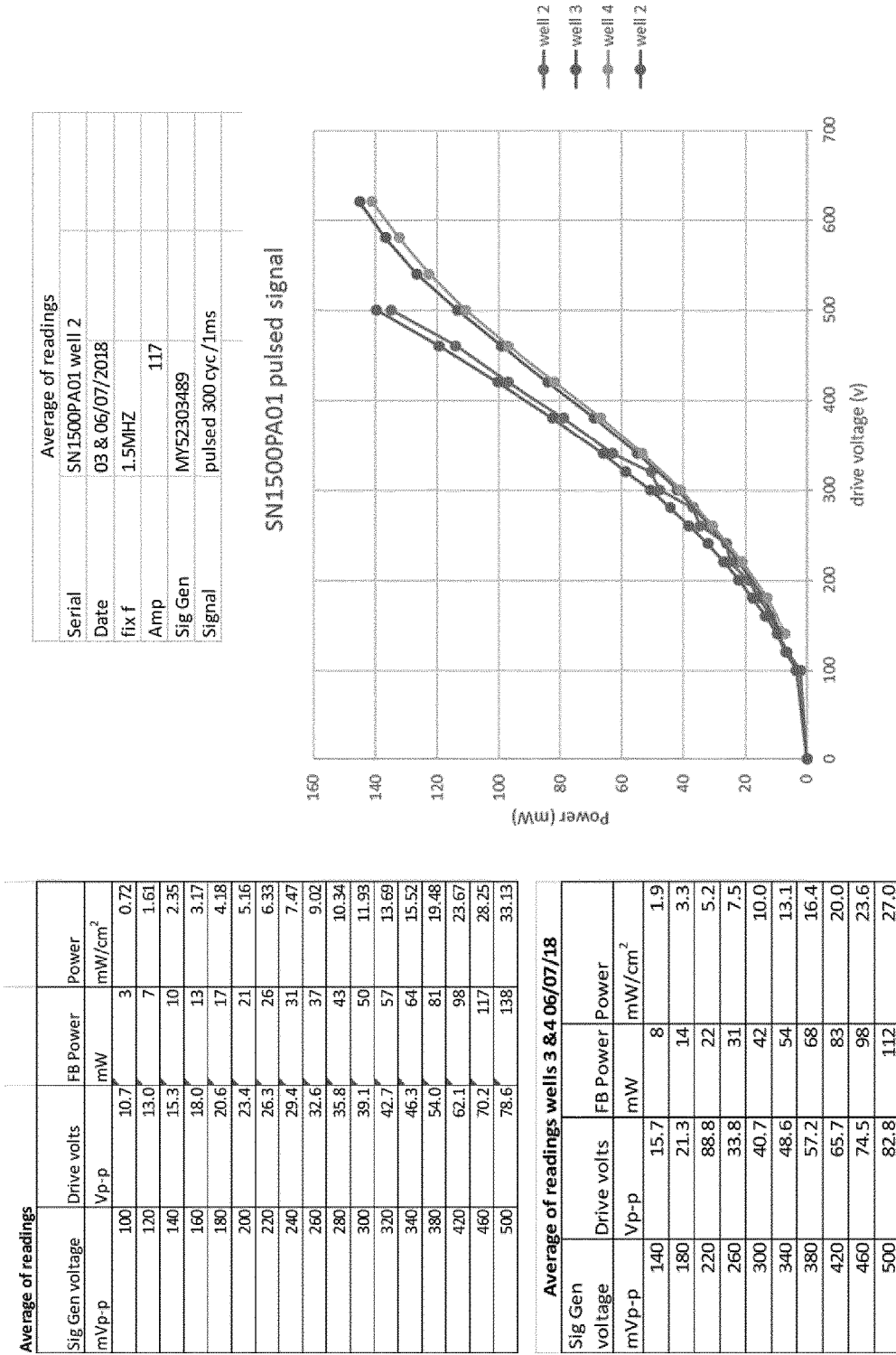
FIGS. 13A-B illustrate embodiments of calibration curves and the accompany data sets for therapeutic ultrasound apparatuses.
Figure 13B:
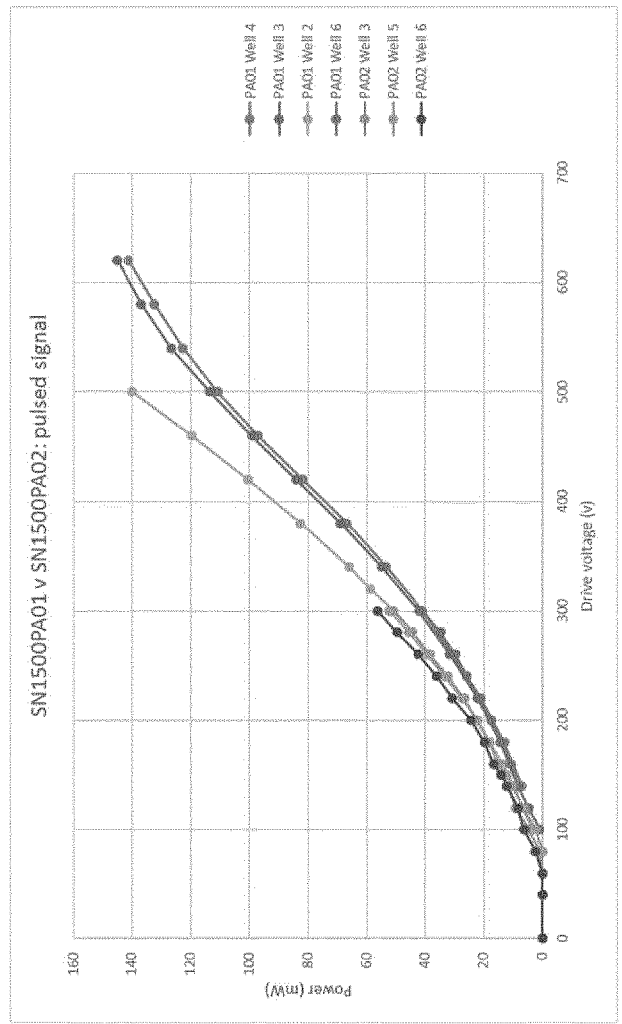

In certain embodiments, the signal may be pulsed, while in some embodiments the signal may be continuous. In some embodiments the duty factor (pulse duration (sec)/pulse repetition period (sec)×100) may be about 10%, about 20%, about 30%, about 40%, about about 50%, about 60%, about 70%, about 80%, about 90%, or about 100%. In some embodiments, the signal may be delivered continuously for about 30 seconds, about 1 minute, about 2 minutes, about 3 minutes, about 4 minutes, about 5 minutes, about 10 minutes, about 15 minutes, about 20 minutes, about 25 minutes, about 30 minutes, or greater than 30 minutes. FIGS. 13A-B depict calibration curves with accompanying data for two different therapeutic ultrasound apparatuses at 1.5 MHz pulsed at 300 cycles/millisecond. The calibration curves show acoustic power output alongside the corresponding input voltage. As described above, one of skill in the art will understand that multiple factors within the therapeutic ultrasound apparatus will alter the output acoustic power.

By means of non-limiting examples, multiple experiments were conducted to determine the effectiveness of a therapeutic ultrasound signal, such as may be used in combination with the therapeutic ultrasound apparatuses of FIGS. 6-12. In brief, a modified fibroblast cell line with an impaired fibronectin Syndecan-4 signaling pathway (the healthy pathway indicated in FIG. 5 above) was treated with ultrasound signals and the PAK phosphorylation was measured. A measurement of PAK phosphorylation is an indication of stimulation of the fibroblasts toward migration and healing activities, as shown above in FIG. 5.

Figure 14:
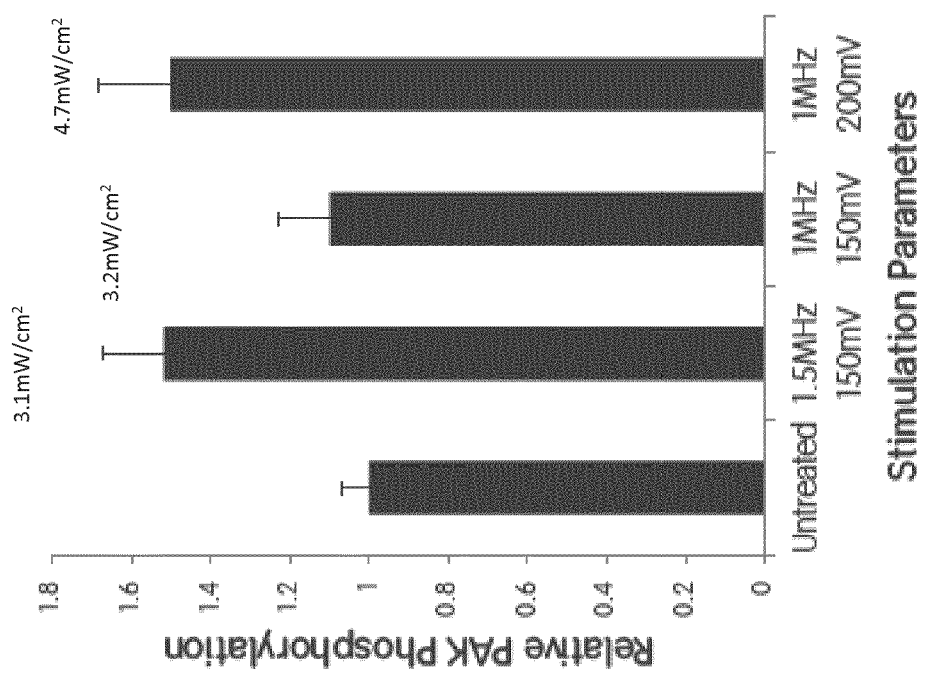
FIG. 14 is a figure depicting the results of a non-limiting experiment involving therapeutic ultrasound.

An example of one such non-limiting experiment is depicted in FIG. 14. Cells treated with a frequency of 1 MHz with acoustic power of 4.7 mW/cm$^2$ and cells treated with a frequency of 1.5 MHz and an acoustic power of 3.1 mW/cm$^2$ showed an increase in PAK phosphorylation compared to untreated cells. Cells treated with 1 MHz and 3.2 mW/cm$^2$ showed a slight increase in PAK phosphorylation as compared to the untreated population, but the effect was minor and may be within the error range. Therefore, cells treated with a higher frequency had the same biochemical output as cells treated at a higher acoustic power but lower frequency, potentially indicating that 1.5 MHz is more desirable than 1.0 MHz.

Figure 15:
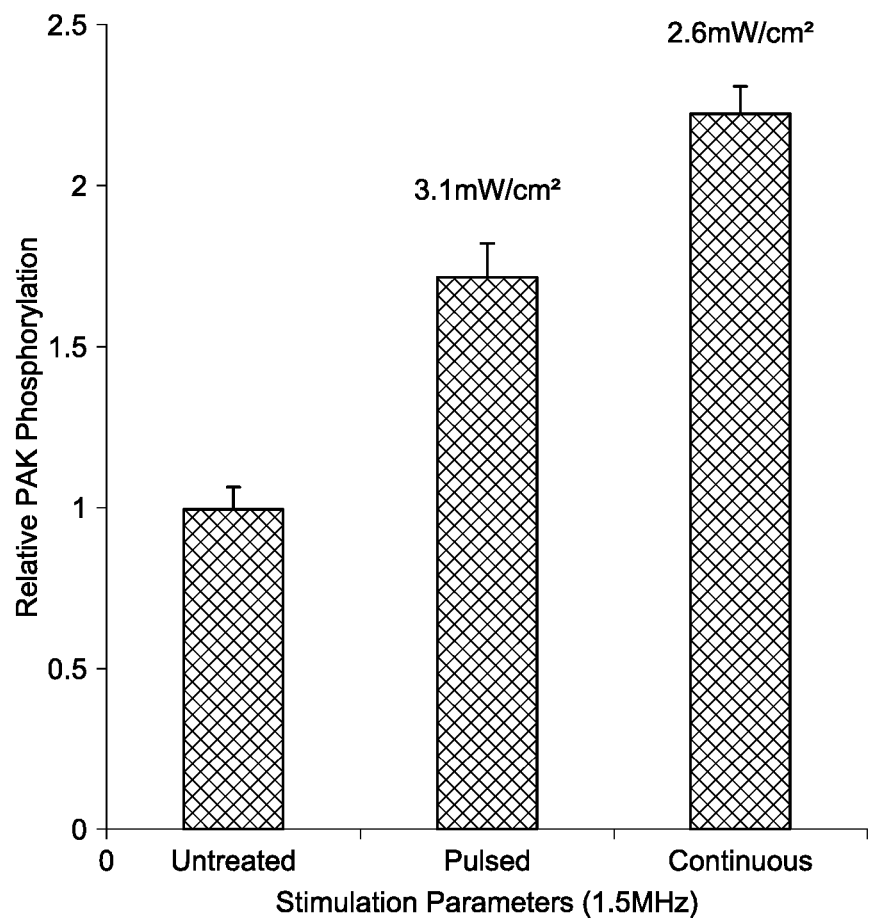
FIG. 15 is a figure depicting the results of a non-limiting experiment involving therapeutic ultrasound.

Another example of a non-limiting experiment involving ultrasound and impaired fibroblasts is depicted in FIG. 15 with a 1.5 MHz frequency signal, similar to the signal produced by the EXOGEN device produced by Bioventus. Here, the pulsed signal was pulsed at an acoustic power of 3.1 mW/cm$^2$ and the continuous signal was delivered with an acoustic power of 2.6 mW/cm$^2$, to simulate a relatively similar amount of vibrational energy delivery (acoustic power). However, even with a lower amount of vibrational energy delivery, the continuous signal produced a greater PAK phosphorylation, indicating that a continuous signal may provide improved wound healing over the pulsed signal.

The results of another such non-limiting experiment involving the impaired fibroblasts described above is shown in FIG. 16. Here, even with increasing power, at 1 MHz, the continuous signal triggers a larger biochemical output as compared to the pulsed signal. However, the biochemical response for the continuous signal did not increase with increasing acoustic power at 1 MHz. This result may indicate a plateauing effect for increases in acoustic power for a continuous signal at 1 MHz.

Figure 17:
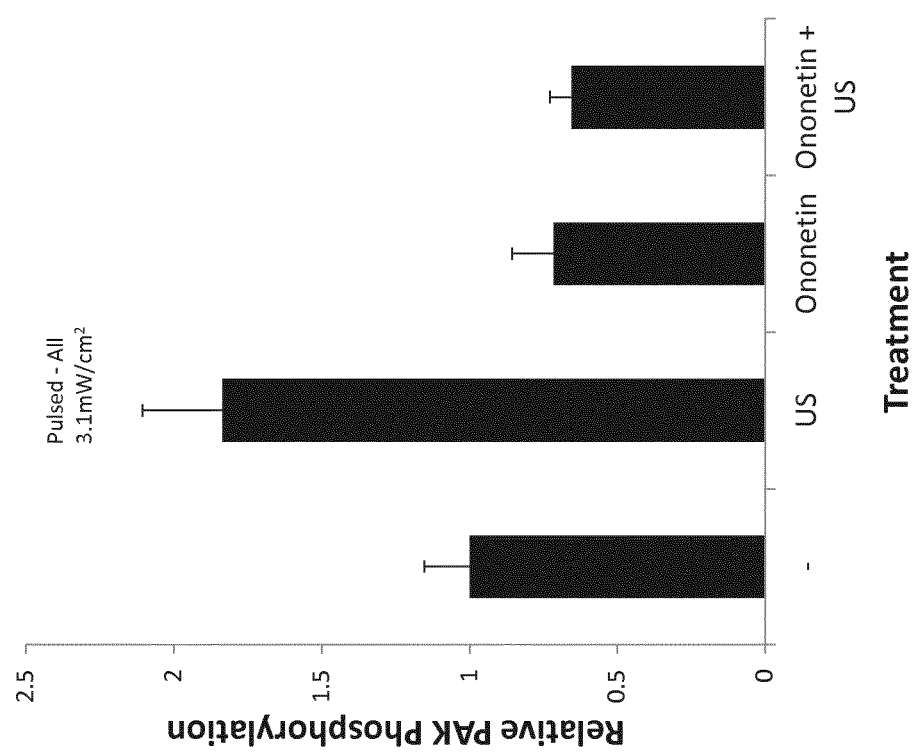
FIG. 17 is a figure depicting the results of a non-limiting experiment involving inhibition of the cellular response to therapeutic ultrasound.
Figure 18:
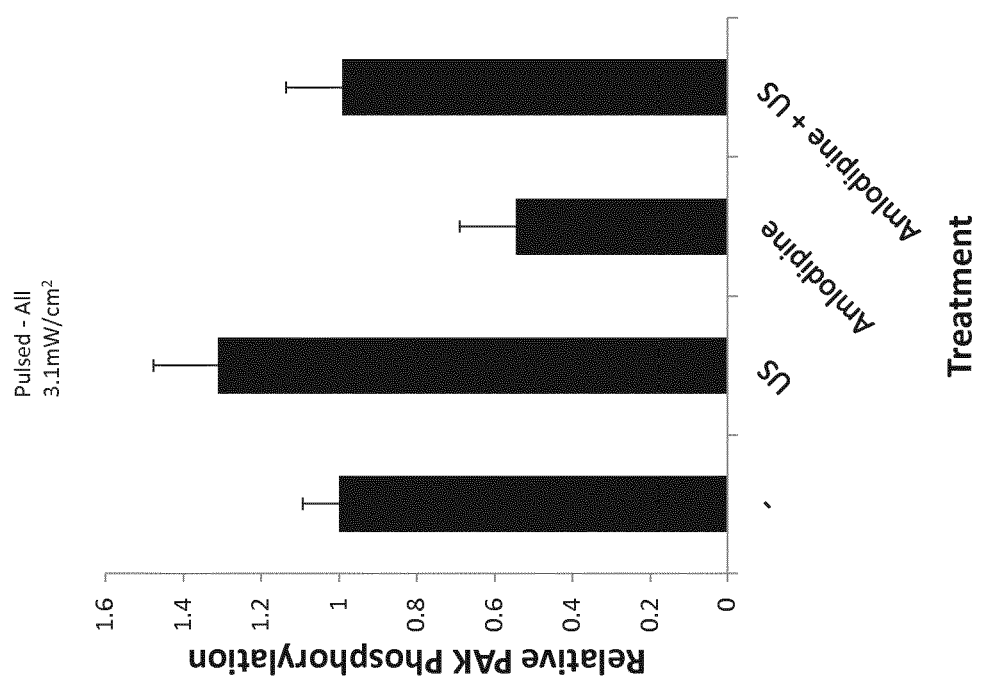
FIG. 18 is a figure depicting the results of a non-limiting experiment involving inhibition of the cellular response to therapeutic ultrasound.

FIGS. 17-18 depict non-limiting experiments using a pulsed signal at 3.1 mW/cm$^2$ involving the impaired fibroblasts described above. Here, the fibroblasts were blocked with various inhibitors and exposed to an ultrasound signal. As depicted in FIG. 17, use of the calcium channel inhibitor Ononetin, which blocks trp-type calcium channels also blocked the ultrasound signal. In contrast, as shown in FIG. 18, the ultrasound signal was not blocked through the use of the L-type calcium channel inhibitor amlodipine. These results suggest that the ultrasound mediated pathway involves a tryp-type calcium channel mediated pathway. These types of pathways are known to be sensitive to mechanical and temperature stimulation, such as may be delivered via vibrational energy.

Figure 19:
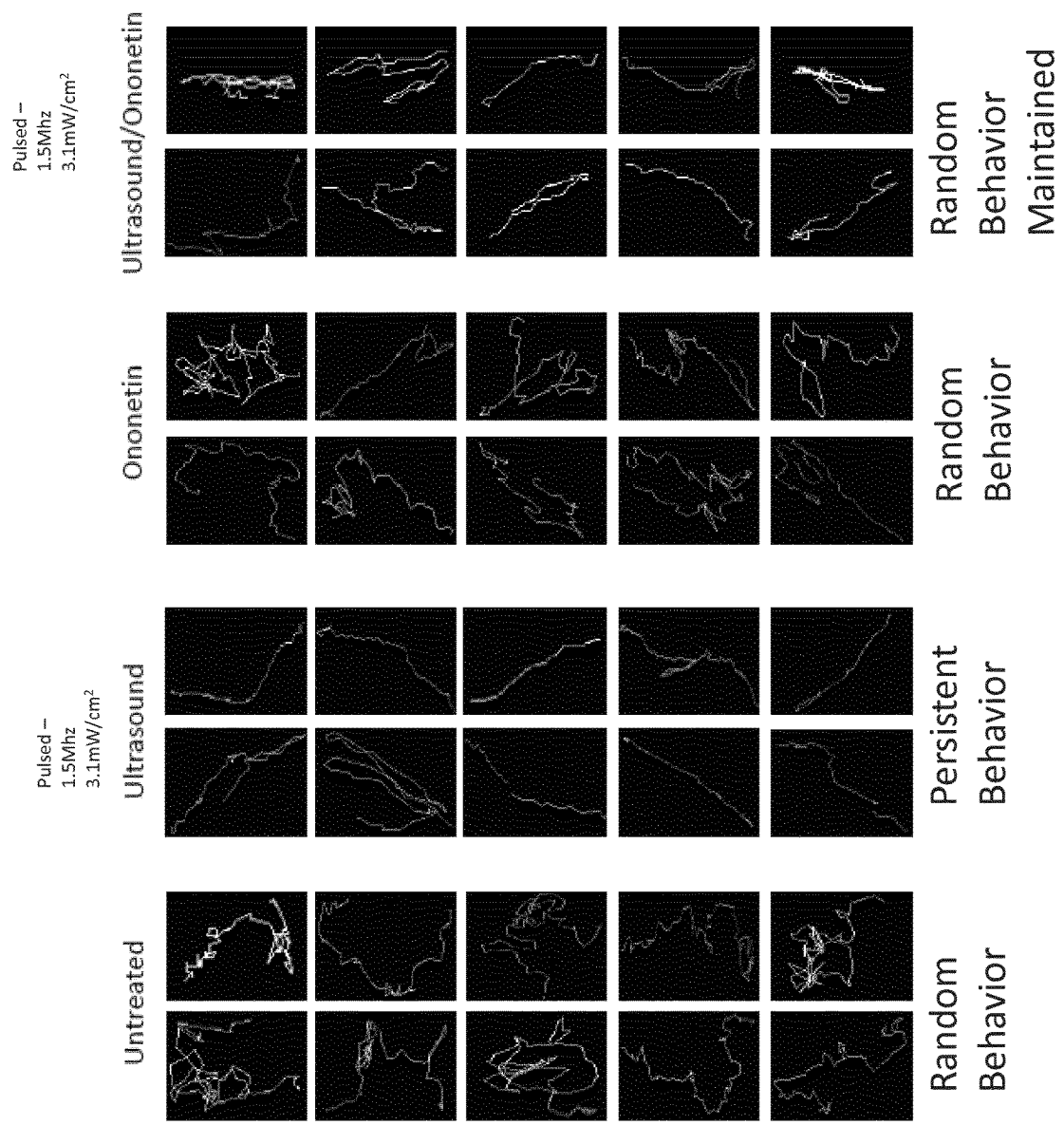
FIG. 19 illustrates the results of a non-limiting experiment involving migration of cells in response to therapeutic ultrasound.

To further support the results of the experiment of FIG. 17, a non-limiting migrational assay experiment was performed using a pulsed signal at 1.5 MHz and 3.1 mW/cm$^2$ to monitor the relative migration of the fibroblasts when subjected to ultrasound with or without Ononetin. Increased migration may be generally indicative of increased healing. As shown in FIG. 19, when untreated, the fibroblasts show a random migration; however, when subjected to ultrasound, the fibroblasts display a controlled migration. However, this effect was lessened by treatment with the inhibitor Ononetin.

Figure 20:
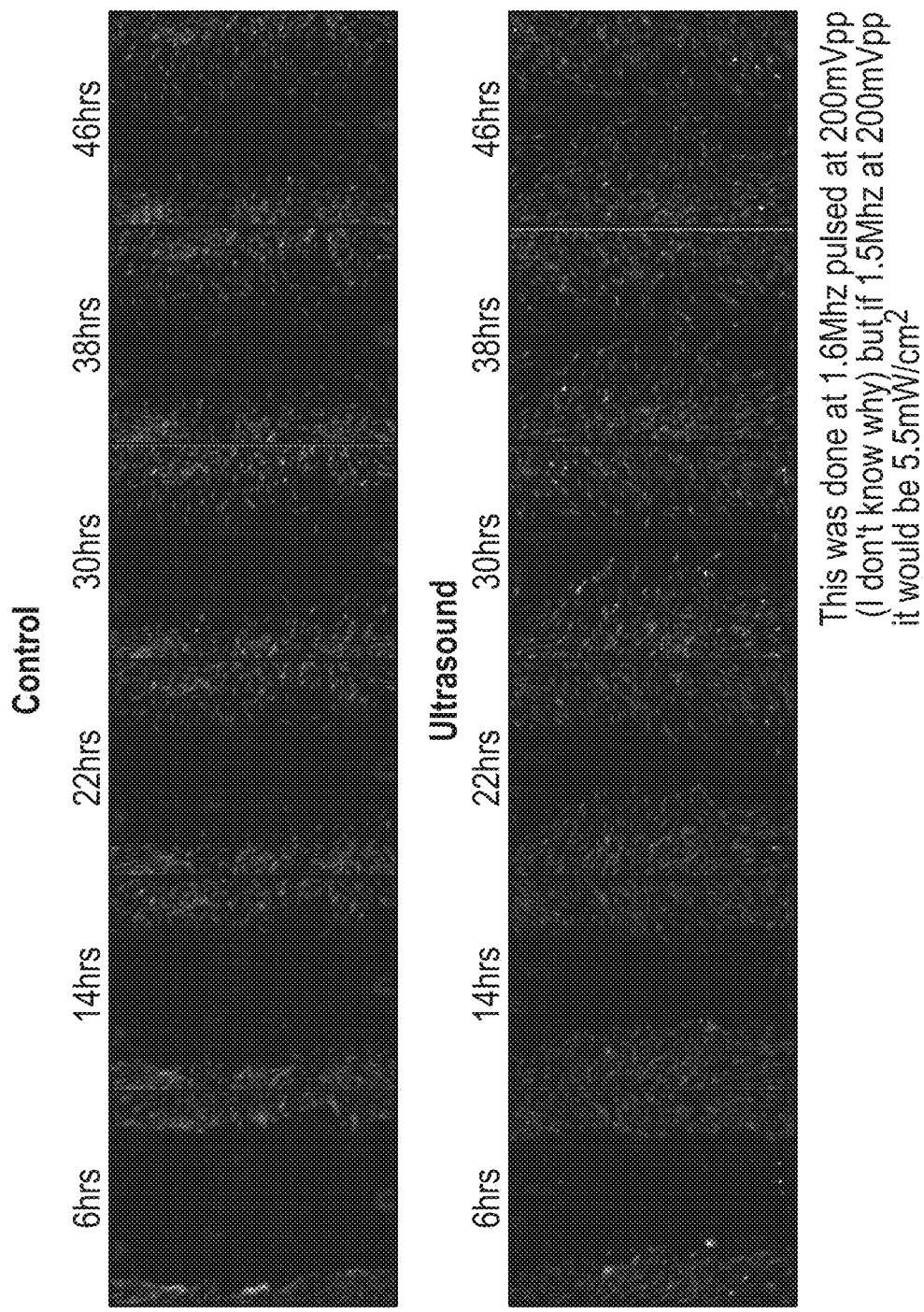
FIG. 20 illustrates the results of a non-limiting experiment involving migration of cells in response to therapeutic ultrasound.

FIG. 20 depicts a non-limiting experiment showing fibroblast migration across a gap over time while being subjected to an ultrasound signal of 1.6 MHz, and approximately 5.5 mW/cm$^2$. Such an experiment is a good proxy for wound healing, as fibroblast migration across a gap may indicate a rate of healing across a wound. As shown in FIG. 20, fibroblast migration across the gap is greatly increased when subjected to ultrasound over 46 hours, thereby indicating the potential for therapeutic ultrasound in wound healing.

Figure 16:
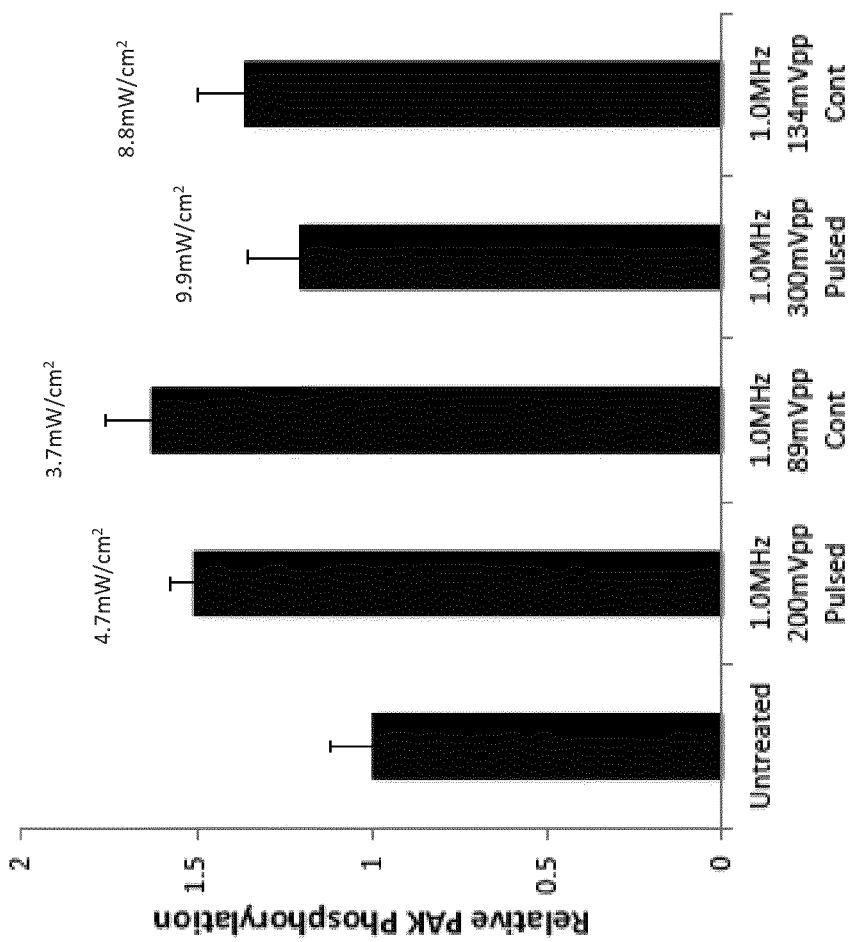
FIG. 16 is a figure depicting the results of a non-limiting experiment involving therapeutic ultrasound.
Figure 21:
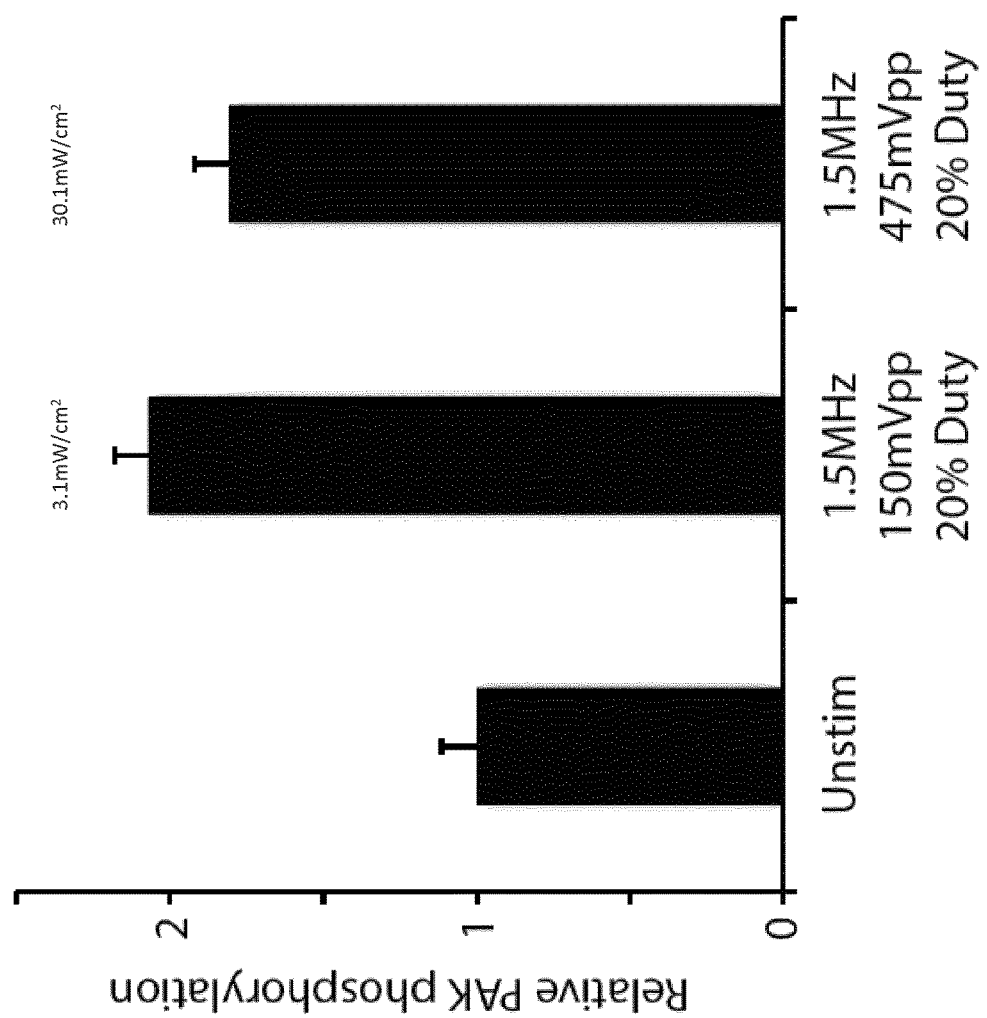
FIG. 21 is a figure depicting the results of a non-limiting experiment involving inhibition of the cellular response to therapeutic ultrasound.

FIG. 21 depicts another example of a non-limiting experiment, similar to the experiments of FIGS. 14 and 16. Here, for this particular set-up with a 20% duty cycle, 150 mVpp corresponds to an acoustic power of approximately 3.1 mW/cm$^2$, while 475 mVpp corresponds to an acoustic power of approximately 30.1 mW/cm$^2$. Here, with a 20% duty cycle, the relative PAK phosphorylation shows a slight decrease at 30.1 mW/cm$^2$ as compared to 3.1 mW/cm$^2$.

Figure 22:
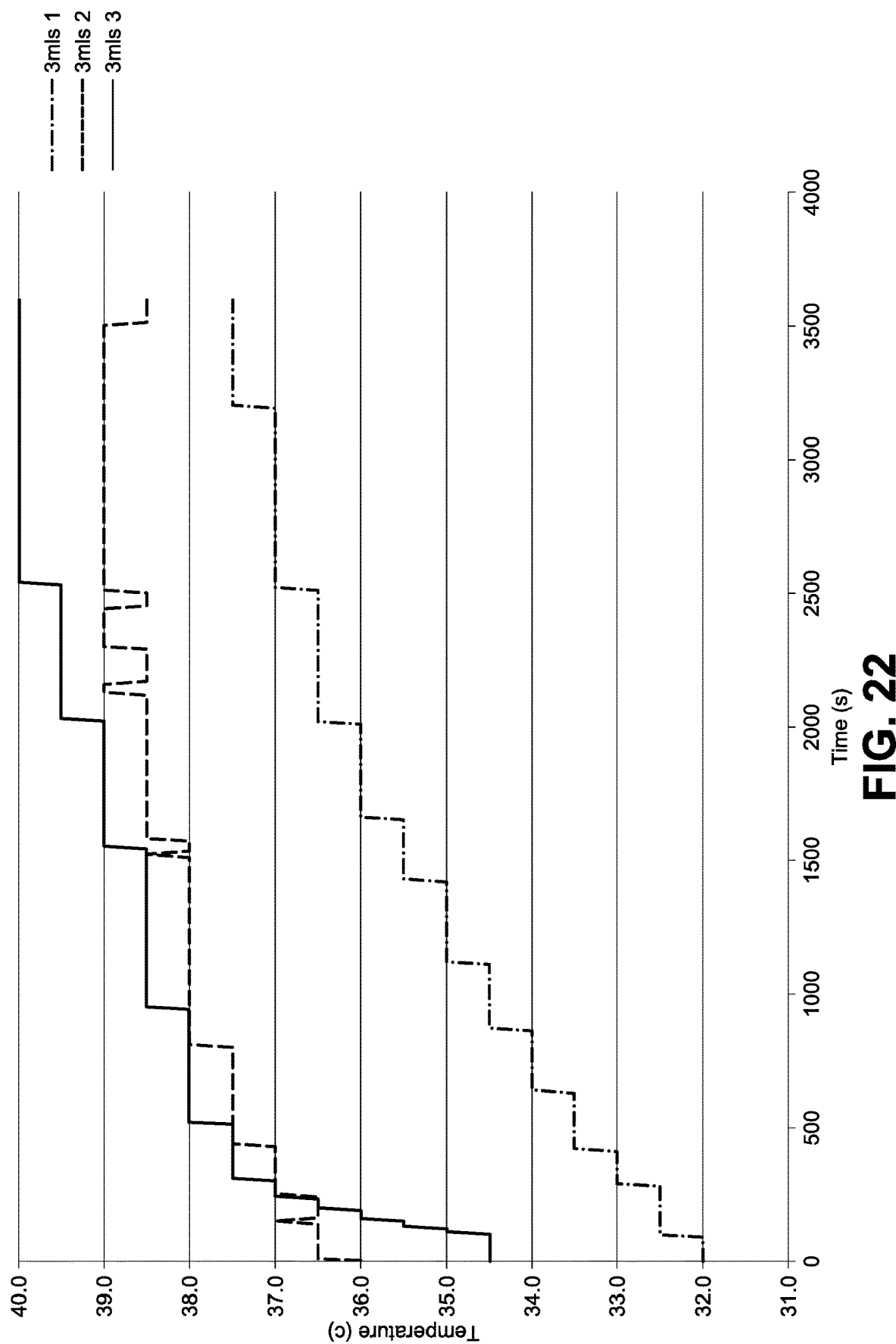
FIG. 22 illustrates the results of a non-limiting experiment involving the effect of duration of therapeutic ultrasound therapy on increases in temperature.

FIG. 22 depicts another example of a non-limiting experiment to assess an increase in temperature with time during ultrasound treatment at 1.5 MHz. Although the individual data replicates are highly variable, the average increase in temperature over the course of 20 minutes of treatment is 4.7 degrees Celsius. Therefore, one of skill in the art will understand that the temperature of an underlying substrate or tissue exposed to therapeutic ultrasound may increase over time during treatment.

Figure 23:
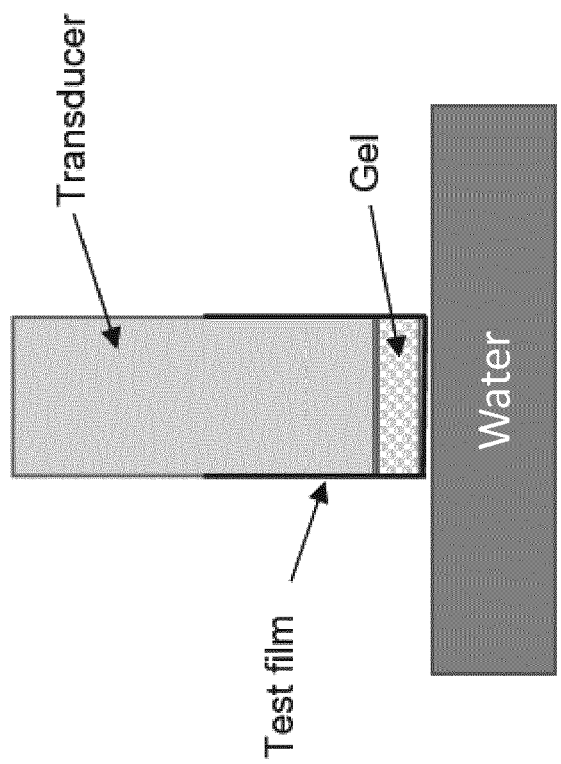
FIG. 23 illustrates a testing setup to evaluate ultrasonic transmission through a film.

FIG. 23 depicts an experimental setup for evaluating the ultrasound transmission of a layer of film. Here, a transducer is placed in direct contact with a transmissive gel, which is then wrapped in a layer of the test film. Ultrasound is then delivered through the gel and the test film into a water bath, where the ultrasound intensity is measures. Such an experiment allows one of skill in the art to assess the ultrasound transmission properties of the film. Table 1 below provides a listing of the various material films tested to generate the data provided in FIGS. 24 and 25. All films listed in Table 1 (below) are constructed from polyurethane.

TABLE 1

| Sample type with batch number | Corresponding sample |
| --- | --- |
| FlexiGrid; 80082574; 16500201 | FlexiGrid 1 + ~5% additive; 30 gsm, 30 um (average mW) |
| EU30; 80082578; 16500381 | FlexiGrid; 32 gsm, 30 um (average mW) |
| EU45; 80082345; 16500561SF | IV3000; 45 gsm, 45 um (average mW) |
| FlexiFix; 80082571; 16500684 | FlexiGrid 2 + ~5% additive; 30 gsm, 30 um (average mW) |
| EU75; 80083061-04; 16500610 | FlexiGrid; 75 gsm, 72 um (average mW) |
| EU51 80083253 Roll 1 R/S | IV3000; 50 gsm, 48 um (average mW) |
| EU40 80082580; 16500291 | FlexiGrid, 40 gsm, 40 um (average mW) |
| EU33 pink AA top film 80082582; 16500537SF | IV3000; 30 gsm, 30 um (average mW) |

Figure 24:
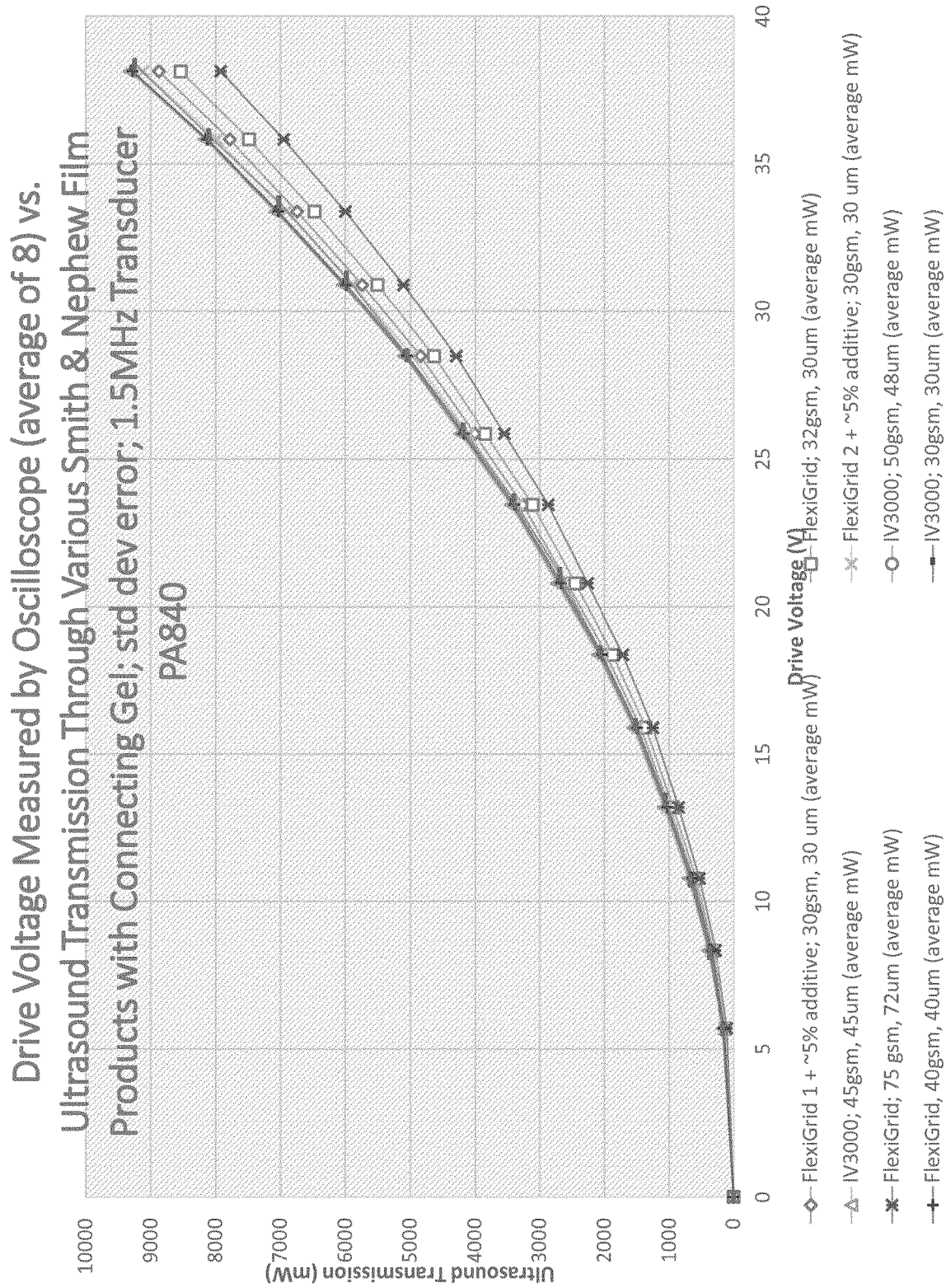
FIG. 24 illustrates the results of a non-limiting experiment to assess the relative increase in ultrasound transmission through various film mediums with increased drive voltage.
Figure 25:
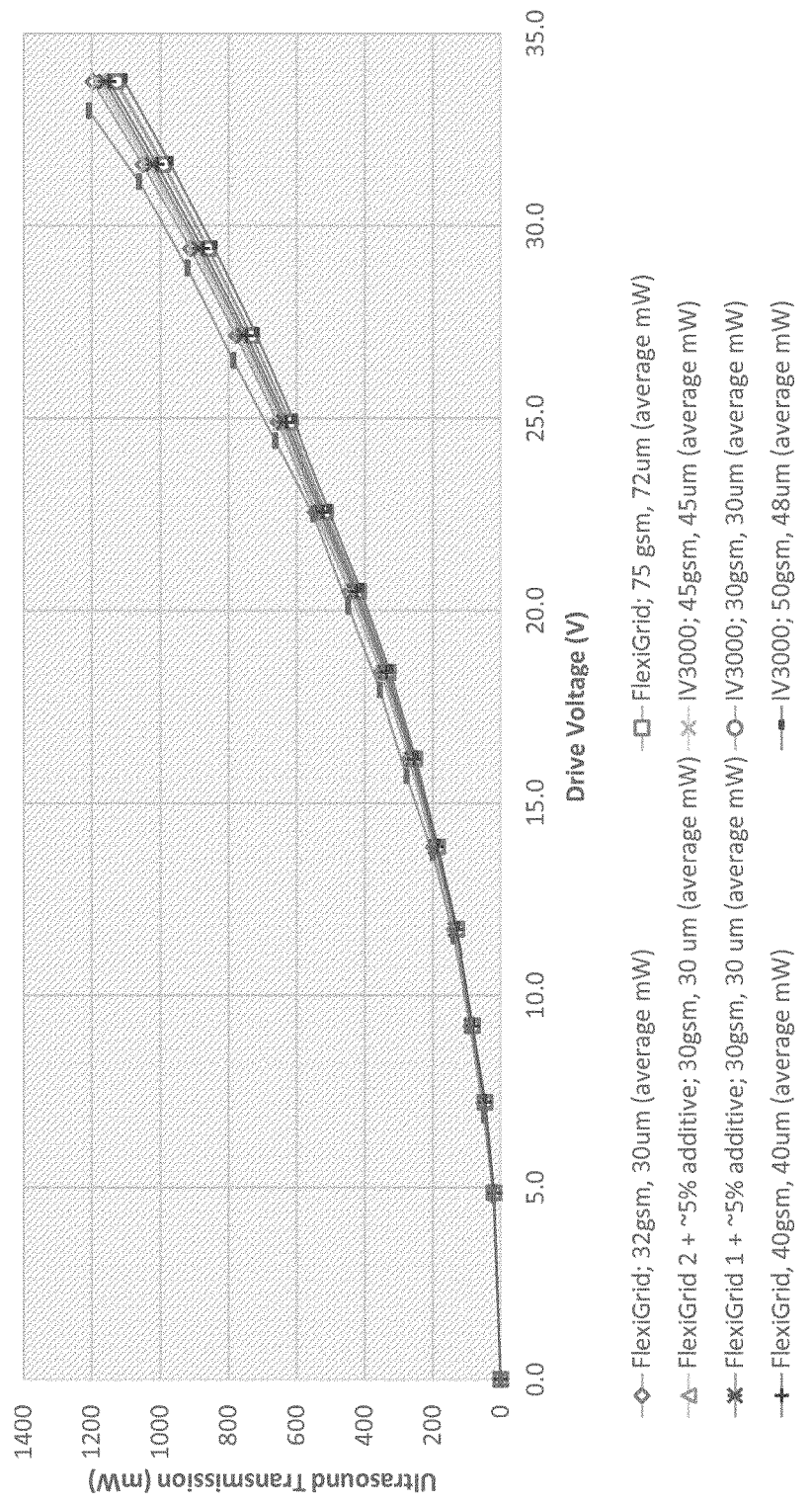
FIG. 25 illustrates the results of a non-limiting experiment to assess the relative increase in ultrasound transmission through various film mediums with increased drive voltage.

FIG. 24 depicts a non-limiting experiment utilizing the films of Table 1 with the transducer and film setup depicted in FIG. 25. Here, at 1.5 MHz, all films showed an increase in ultrasound transmission power as drive voltage was increased. However, polyurethane film "IV3000," 45 gsm, 45 um showed the highest increase in ultrasound power with increasing drive voltage, while polyurethane film FlexiGrid, 40 gsm, 40 um (average mW) showed the smallest increase in power with increasing drive voltage.

FIG. 25 depicts a non-limiting experiment utilizing the films of Table 1 with the transducer and film setup depicted in FIG. 25, similar to the experiment of FIG. 26. Here, at 3.0 MHz, all films showed an increase in ultrasound transmission power as drive voltage was increased. Polyurethane film FlexiGrid 32 gsm, 30 um (average mW) showed the highest increase in ultrasound power with increasing drive voltage, while polyurethane film IV3000; 50 gsm, 48 um (average mW) showed the lowest increase in ultrasound power with increasing drive voltage.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A method of treating a wound with vibrational energy, comprising:
    applying vibrational energy to a wound from an ultrasonic transducer, the ultrasonic transducer positioned within an absorbent wound dressing, the dressing comprising:
    a wound contact layer, and
    a delivery layer positioned above the wound contact layer, the delivery layer comprising a porous portion and a transmission portion, the transmission portion comprising a transmission material configured to transmit vibrational energy; and
    controlling the ultrasonic transducer such that vibrational energy is delivered to the wound, the vibrational energy delivered at an acoustic power of about 3 mW/cm$^2$ and a frequency of about 1.5 MHZ.

2. The method of claim 1, wherein controlling the ultrasonic transducer comprises controlling the ultrasonic transducer such that vibrational energy is delivered continuously to the wound for a period of time greater than 1 minute.

3. The method of claim 2, wherein the vibrational energy is delivered continuously for at least about 20 minutes.

4. The method of claim 1, wherein the vibrational energy is pulsed to the wound.

5. The method of claim 1, wherein the vibrational energy comprises a duty factor of about 20%.

6. The method of claim 1, further comprising applying negative pressure to the wound.

7. The method of claim 1, further comprising collecting wound exudate in an absorbent layer within the wound dressing.

* * * * *

UNITED STATES PATENT AND TRADEMARK OFFICE
CERTIFICATE OF CORRECTION

Page 1 of 2

PATENT NO. : 12,403,044 B2
APPLICATION NO. : 17/285723
DATED : September 2, 2025
INVENTOR(S) : Mark Darren Bass et al.

It is certified that error appears in the above-identified patent and that said Letters Patent is hereby corrected as shown below:

On the Title Page

Column 1 item (71) (Applicant), Line 1, delete "T.J. Smith and Nephew, Limited" and insert -- T.J.Smith and Nephew,Limited --.

Column 1 item (73) (Assignee), Line 1, delete "T.J. Smith and Nephew, Limited" and insert -- T.J.Smith and Nephew,Limited --.

In the Specification

Column 5, Line 37, delete "trauma, sterniotomies," and insert -- trauma, sternotomies, --.

Column 7, Line 51, delete "bacterial bather." and insert -- bacterial barrier. --.

Column 8, Line 15, delete "dressing is maybe" and insert -- dressing is may be --.

Column 11, Line 33, delete "dressing ofthis" and insert -- dressing of this --.

Column 13, Line 22, delete "760 mmHg" and insert -- 760 mmHg. --.

Column 13, Line 25, delete "–200 mmHg Note" and insert -- –200 mmHg. Note --.

Column 13, Line 30, delete "–150 mmHg Alternatively" and insert -- –150 mmHg. Alternatively --.

Column 14, Line 62, delete "pentetration, amputation," and insert -- penetration, amputation, --.

Column 15, Line 40, delete "of spascity and" and insert -- of spasticity and --.

Signed and Sealed this
Twenty-seventh Day of January, 2026

John A. Squires
*Director of the United States Patent and Trademark Office*

Column 16, Line 12, delete "be Renays Soft" and insert -- be Renasys Soft --.

Column 17, Line 5, delete "–150 mmHg Alternatively" and insert -- –150 mmHg. Alternatively --.

Column 21, Line 64, delete "(bacterial bather) and" and insert -- (bacterial barrier) and --.

Column 28, Line 62, delete "terms oftiming of" and insert -- terms of timing of --.

Column 31, Line 61, delete "about about 50%," and insert -- about 50%, --.

Column 34, Line 35, delete "certain ofthe steps" and insert -- certain of the steps --.